(12) United States Patent
Maurice et al.

(10) Patent No.: US 10,947,260 B2
(45) Date of Patent: Mar. 16, 2021

(54) PHOSPHINOLACTONE DERIVATIVES AND PHARMACEUTICAL USES THEREOF

(71) Applicants: INSTITUT NATIONAL DE LA SANTE ET DE LA RECHERCHE MEDICALE (INSERM), Paris (FR); ECOLE PRATIQUE DES HAUTES ETUDES, Paris (FR); ECOLE NATIONALE SUPERIEURE DE CHIMIE DE MONTPELLIER, Montpellier (FR); CENTRE NATIONAL DE LA RECHERCHE SCIENTIFIQUE, Paris (FR); UNIVERSITÉ DE MONTPELLIER, Montpellier (FR)

(72) Inventors: Tangui Maurice, Saint-Gély-du-Fesc (FR); Jean-Noël Volle, Jacou (FR); David Virieux, Saint-Gély-du-Fesc (FR); Jean-Luc Pirat, Montpellier (FR); Coralie Laborde, Poussan (FR)

(73) Assignees: INSTITUT NATIONAL DE LA SANTE ET DE LA RECHERCHE MEDICALE (INSERM), Paris (FR); ECOLE PRATIQUE DES HAUTES ETUDES, Paris (FR); ECOLE NATIONALE SUPERIEURE DE CHIMIE DE MONTPELLIER, Montpellier (FR); CENTRE NATIONAL DE LA RECHERCHE SCIENTIFIQUE, Paris (FR); UNIVERSITÉ DE MONTPELLIER, Montpellier (FR)

( * ) Notice: Subject to any disclaimer, the term of this patent is extended or adjusted under 35 U.S.C. 154(b) by 0 days.

(21) Appl. No.: 16/097,914

(22) PCT Filed: Apr. 27, 2017

(86) PCT No.: PCT/EP2017/060129
§ 371 (c)(1),
(2) Date: Oct. 31, 2018

(87) PCT Pub. No.: WO2017/191034
PCT Pub. Date: Nov. 9, 2017

(65) Prior Publication Data
US 2019/0144476 A1 May 16, 2019

(30) Foreign Application Priority Data
May 2, 2016 (FR) ...................... 1653960

(51) Int. Cl.
C07F 9/6584 (2006.01)
A61P 25/28 (2006.01)
(52) U.S. Cl.
CPC ............ *C07F 9/6584* (2013.01); *A61P 25/28* (2018.01)

(58) Field of Classification Search
None
See application file for complete search history.

(56) References Cited

U.S. PATENT DOCUMENTS 8,383,609 B2 * 2/2013 Pirat ...................... A61P 35/00
514/100

OTHER PUBLICATIONS

Pirat J L et al: "Pallado-catalysed P-arylations and P-vinylation of 2-hydrogeno-2-oxo-1,4,2-oxazaphosphinanes", Tetrahedron, Elsevier Science Publishers, Amsterdam, NL, vol. 61, No. 29, Jul. 18, 2005 (Jul. 18, 2005), pp. 7029-7036, XP027861194, ISSN: 0040-4020, [retrieved on Jul. 18, 2005] *.
Jean-Noël Volle et al: "Drug discovery: phosphinolactone, in vivo bioisostere of the lactol group", Organic & Biomolecular Chemistry, vol. 8, No. 6, Jan. 1, 2010 (Jan. 1, 2010), GB, pp. 1438, XP055332345, ISSN: 1477-0520, DOI: 10.1039/b919345f *.
Volle J N et al: "Chiral phosphinyl analogues of 2-C-arylmorpholinols: 2-aryl-3,5-diphenyl-[1,4,2]-oxazaphosphinanes", Tetrahedron Asymmetry, Pergamon Press Ltd, Oxford, GB, vol. 17, No. 9, May 15, 2006 (May 15, 2006), pp. 1402-1408, XP024962074, ISSN: 0957-4166, [retrieved on May 15, 2006], DOI: 10.1016/J.Tetasy.2006.05.003 *.
Cristau H J et al: "Synthesis, reactivity and stereochemistry of new phosphorus heterocycles with 5- or 6- membered rings", Journal of Organometallic Chemistry, Elsevier-Sequoia S.A. Lausanne, CH, vol. 690, No. 10, May 16, 2005 (May 16, 2005), pp. 2472-2481, XP027708585, ISSN: 0022-328X, [retrieved on May 16, 2005] *.

(Continued)

*Primary Examiner* — Kamal A Saeed
(74) *Attorney, Agent, or Firm* — Nixon & Vanderhye

(57) ABSTRACT

A compound of following formula (I):

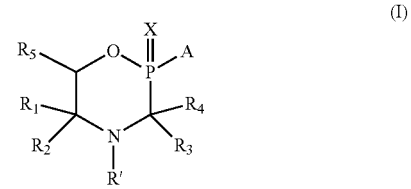

Figure 1:
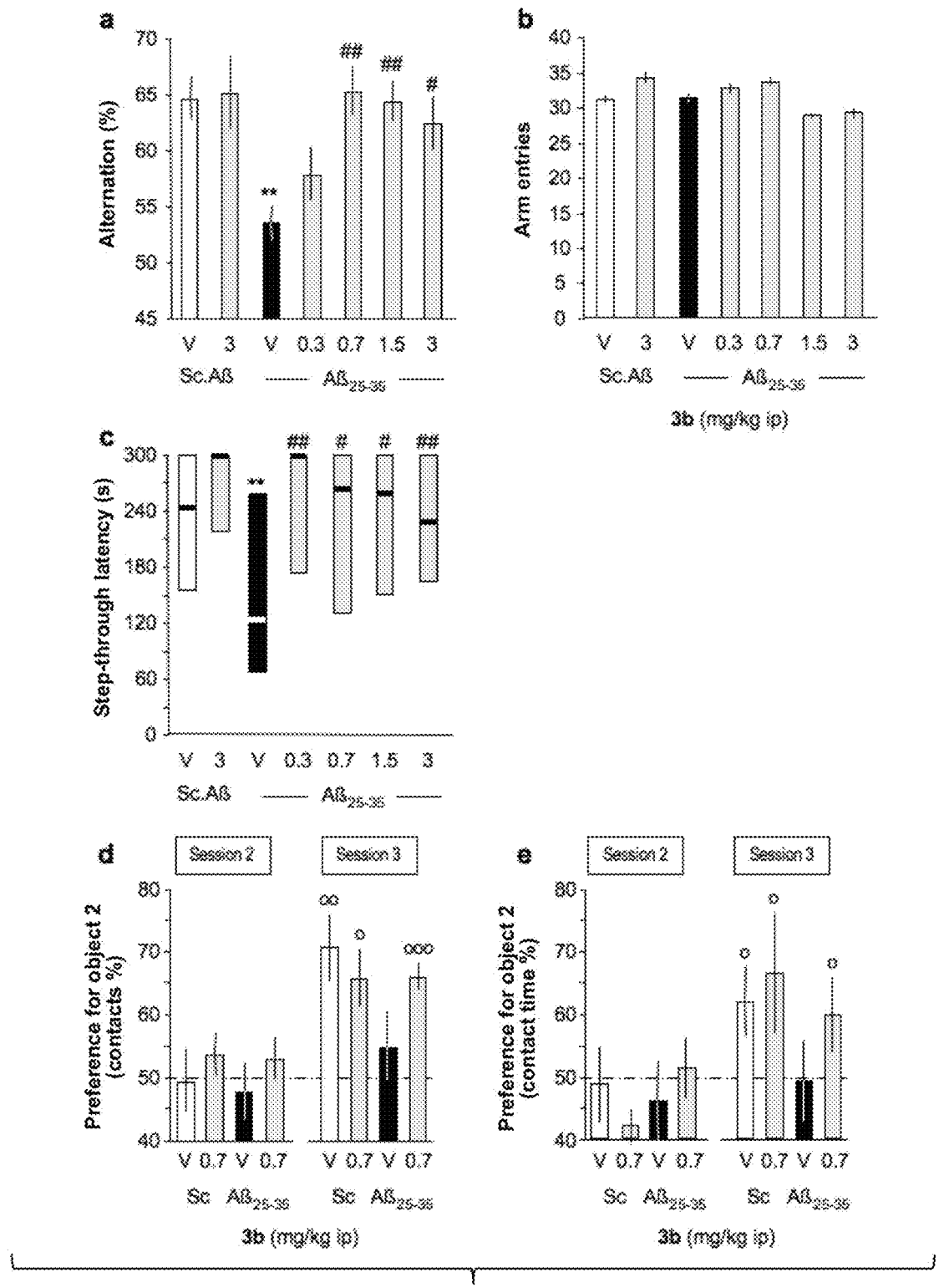

where:
X is O or S;
A is an aromatic (hetero)cycle having 5 to 10 atoms selected from among carbon and nitrogen atoms, optionally being substituted;
R' is H or ($C_1$-$C_6$)alkyl group;
$R_1$, $R_2$, $R_3$, $R_4$ and $R_5$, the same or different, are selected from the group formed by: H, ($C_1$-$C_6$)alkyl groups and ($C_6$-$C_{10}$)aryl groups.
The compound is for the treatment of neurodegenerative diseases.

15 Claims, 13 Drawing Sheets

(56) References Cited

OTHER PUBLICATIONS

A. Van Der Lee et al: "Structure-directing weak phosphoryl X H...O=P(X=C, N) hydrogen bonds in cyclic oxazaphospholidines and oxazaphosphinanes", Acta Crystallographica. Section B, Structural Science, vol. 64, No. 2, Mar. 14, 2008 (Mar. 14, 2008), DK, pp. 196-205, XP055332343, ISSN: 0108-7681, DOI: 10.1107/S0108768107061770 *.

Jean-Noël Volle et al: "Phosphono- and Phosphinolactones in the Life Sciences", pp. 129-193, XP055332311, DOI: 10.1016/bs.aihch.2015.10.004, "Advances in Heterocyclic Chemistry", vol. 118, Jan. 7, 2016, Academic Press, ISSN: 0065-2725, article*.

Jrme Monbrun et al: "Diastereoselective Michael addition of 2-2-oxo-1,4,2-oxaza phosphinanes to olefins", Tetrahedron, Elsevier Science Publishers, Amsterdam, NL, vol. 67, No. 2, Oct. 26, 2010 (Oct. 26, 2010), pp. 540-545, XP028165023, ISSN: 0040-4020, [retrieved on Nov. 12, 2010], DOI: 10.1016/J. TET.2010.10.078 *.

Volle et al: "Phosphinyl analogues of hydroxybupropion: (+/-)-2-aryl-3,3,5,5-tetramethyl-[1,4,2]-oxazaphosphinanes", Tetrahedron Letters, Elsevier, Amsterdam, NL, vol. 48, No. 27, Jun. 7, 2007 (Jun. 7, 2007), pp. 4695-4697, XP022107524, ISSN: 0040-4039, DOI: 10.1016/J.TETLET.2007.05.014 *.

Fagadar-Cosma et al: "Phosphorus compounds acting as plant hormones", vol. 15, No. 2, Jan. 1, 2006 (Jan. 1, 2006), pp. 151-158, XP008182743, ISSN: 1224-9513, Retrieved from the Internet <URL:http://www.chimie.uvt.ro/awut_sc/awut/Z_Cont&Summary_Vol%2015%282%29%202006.pdf> *.

Rendie Liu et al: "Efficient One-Pot Synthesis of Novel Spirooxindole-Fused Phosphorous Heterocycle Derivatives by a Three-Component Domino Reaction", Heteroatom Chemistry, vol. 25, No. 3, Mar. 21, 2014 (Mar. 21, 2014), US, pp. 140-146, XP055332346, ISSN: 1042-7163, DOI: 10.1002/hc.21146 *.

Mudaris Dimukhametov et al: "Synthesis and Crystal Structure of 2-Substituted 3-Aryl-2-Oxophenylbenzo [E ]-1,4,2-Oxazaphosphinanes", Phosphorus, Sulfur and Silicon and the Related Elements, vol. 190, No. 5-6, Jun. 3, 2015 (Jun. 3, 2015), US, pp. 943-946, XP055332349, ISSN: 1042-6507, DOI: 10.1080/10426507.2014.993756 *.

M N Dimukhametov et al: "A convenient synthesis and spatial structure of 22aryl122oxoo22phenylbenzo[e]] 1,4,22oxazaphosphinanes*", Russian Chemical Bulletin International Edition, Jan. 1, 2013 (Jan. 1, 2013), pp. 1882-1891, XP055332351, Retrieved from the Internet <URL:http://rd.springer.com/content/pdf/10.1007/s11172-013-0271-2.pdf> [retrieved on Jan. 5, 2017] *.

Eugenia Fagadar-Cosma et al: "Synthesis, characterization and correlative biological effects in wheat of a benzoxaza- and a diaza-phosphorus(V) heterocycles", Journal of the Serbian Chemical Society, vol. 71, No. 10, Jan. 1, 2006 (Jan. 1, 2006), Belgrade, pp. 1031-1038, XP055332339, ISSN: 0352-5139, DOI: 10.2298/JSC0610031F *.

Jia Zhou et al: "Studies on Cyclic [alpha]-Aminoalkanephosphonate Compounds: A Novel Synthesis of Phenyl-1,4,2-Benzoxaza (or diaza)phosphorin 2-Oxides", Synthesis, vol. 1999, No. 1, Jan. 1, 1999 (Jan. 1, 1999), Stuttgart, DE., pp. 40-42, XP055332338, ISSN: 0039-7881, DOI: 10.1055/s-1999-3676 *.

International Search Report, dated May 24, 2017, from corresponding PCT/EP2017/060129 application.

FR Search Report, dated Jan. 18, 2017, from corresponding FR1653960 application.

* cited by examiner

PHOSPHINOLACTONE DERIVATIVES AND PHARMACEUTICAL USES THEREOF

The subject of the present invention concerns novel compounds, derivatives of phosphinolactones, and the uses particularly pharmaceutical uses thereof, and more particularly for the treatment of neurodegenerative diseases.

A further subject of the invention concerns pharmaceutical compositions containing said compounds.

At the present time, phosphinolactone analogues of hydroxybupropion are known which were synthesized for the purpose of developing novel antidepressants. These compounds have been tested on animal models for depression-related response and have shown significant antidepressant action by reducing the immobility time of mice subjected to the forced swim test.

Neurodegenerative diseases such as Alzheimer's disease, Parkinson's disease, Huntington's disease or amyotrophic lateral sclerosis are chronic invalidating diseases of slow, discrete progression. They generally cause deteriorated functioning of nerve cells, neurons in particular, leading to cell death (or neurodegeneration). The disorders induced by neurodegenerative diseases are varied and can be of cognitive-behavioural, sensory and motor type.

As and when research progresses, numerous similarities have become apparent linking these diseases to each other, especially at cell level and in particular through atypical protein assemblies and induced neuronal death. The discovery of these similarities brings the hope of therapeutic breakthroughs which could simultaneously improve numerous diseases.

Alzheimer's disease is a neurodegenerative disease of slow progression which gradually deteriorates neurons in the brain regions involved in memory, learning and reasoning. It is characterized by extracellular accumulation of β-amyloid peptide (Aβ), forming amyloid plaques in the brain.

At the current time it is estimated that about 3% of persons aged between 65 and 74 years have Alzheimer's disease, and up to about one half of persons aged 85 and over.

There is therefore a current need for effective compounds to treat neurodegenerative diseases, and Alzheimer's disease in particular.

It is the objective of the present invention to provide novel compounds that are particularly effective for the treatment of neurodegenerative diseases.

The present invention therefore concerns a compound of following formula (I):

$$
\begin{array}{c}
\text{(I)} \\
R_5\text{—O—P(=X)—A} \\
R_1\text{—}\ \ \text{—}R_4 \\
R_2\text{—N—}R_3 \\
\ \ \ \ R'
\end{array}
$$

where:
X is O or S;
A is selected from the group formed by:
 $(C_6-C_{10})$aryl groups,
 heteroaryl groups having 5 to 10 atoms, and
 heterocycloalkyls having 5 to 10 atoms,
said aryl, heteroaryl and heterocycloalkyl groups optionally being substituted by at least one substituent selected from the group formed by halogen atoms, $OR_a$, $SR_a$, $NO_2$, $NR_aR_b$, $N(R_a)COOR_c$, $R'_a$ and $OR'_a$;
$R_a$ and $R_b$, the same or different, being H or $(C_1-C_6)$alkyl group;
$R_C$ being a —$(C_1-C_6)$alkylene-$(C_6-C_{10})$aryl radical, in particular a —$CH_2$—$(C_6-C_{10})$aryl radical;
$R'_a$ being selected from among the groups $CF_3$, $CHF_2$ and $CH_2F$;
R' is H or $(C_1-C_6)$alkyl group;
$R_1$, $R_2$, $R_3$, $R_4$ and $R_5$, the same or different, are selected from the group formed by:
 H,
 $(C_1-C_6)$alkyl groups,
 $(C_6-C_{10})$aryl groups,
$R_1$ and $R_2$, together with their carrier carbon atom, able to form a spiran ring having 3 to 6 carbon atoms, and/or
$R_3$ and $R_4$, together with their carrier carbon atom, able to form a spiran ring having 3 to 6 carbon atoms.

for use thereof to treat neurodegenerative diseases.

The compounds of formula (I) may comprise one or more asymmetric carbon atom. They can therefore exist in the form of enantiomers or diastereoisomers. These enantiomers, diastereoisomers, and mixtures thereof including racemic mixtures, form part of the invention.

The compounds of formula (I) can exist as bases or acid addition salts. Said addition salts form part of the invention.

These salts can be prepared with pharmaceutically acceptable acids, but the salts of other acids, useful for example for purification or isolation of the compounds of formula (I), also form part of the invention.

In the present invention, by $C_t-C_z$ is meant a carbon chain having t to z carbon atoms.

According to the invention, the term «halogen atom» designates the atoms of fluorine chlorine, bromine or iodine.

In the present invention, by «alkyl group» is meant an aliphatic, linear or branched, saturated hydrocarbon group, having 1 to 6 carbon atoms unless otherwise indicated. As examples, mention can be made of the methyl, ethyl, n-propyl, isopropyl, butyl, isobutyl, tertbutyl or pentyl groups.

In the present invention, by «—$(C_1-C_6)$alkylene radical» is meant a bivalent, linear or branched radical having 1 to 6 carbon atoms, corresponding to an alkyl group with one hydrogen atom less.

In the present invention, by «aryl group» is meant a cyclic aromatic group having between 6 and 10 carbon atoms. As examples of aryl groups, the phenyl or naphthyl groups can be cited.

In the present invention, by «heteroaryl group» is meant an aromatic monocyclic or bicyclic group with 5 to 10 members containing 1 to 4 heteroatoms selected from among O, S or N. As examples, the following groups can be mentioned: imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinoleinyl, isoquinoleinyl.

As heteroaryl having 5 to 6 atoms, including 1 to 4 nitrogen atoms, particular mention can be made of the following representative groups: pyrrolyl, pyrazolyl, 1,2,3-triazolyl, 1,2,4-triazolyl, tetrazolyl, 1,2,3-triazinyl.

As heteroaryl, mention can also be made of thiophenyl, oxazolyl, furazanyl, 1,2,4-thiadiazolyl, naphthyridinyl, quinoxalinyl, phtalazinyl, imidazo[1,2-a]pyridine, imidazo[2,1-b]thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindole, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, and the corresponding groups derived from fusion thereof or fusion with the phenyl nucleus.

In the present invention, by «heterocycloalkyl group is meant a monocyclic or bicyclic group, saturated or partly unsaturated having 5 to 10 members, comprising one to three heteroatoms selected from among O, S or N. In the invention, the heterocycloalkyl group is attached to the remainder of the molecule via a carbon atom or via a heteroatom and the term bicyclic heterocycloalkyl includes fused bicyclic rings and rings of spiro type.

As saturated heterocycloalkyl having 5 to 6 atoms, mention can be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl or isoxazolidinyl.

If the heterocycloalkyl is substituted, the substitution(s) can be on carbon atom(s) and/or on the heteroatom(s). If the heterocycloalkyl comprises several substituents, these can be carried by one same atom or by different atoms.

The compounds of formula (I) such as defined above are used for the treatment of neurodegenerative diseases.

In the invention, the term «neurodegenerative disease» designates a disease caused by deterioration of the central nervous system and can be identified by neuronal death. The death of the neuron cells observed in neurodegenerative diseases is often preceded by neuronal dysfunction, sometimes for several years.

The term «neurodegenerative disease» therefore includes pathologies or disorders characterized by neuronal dysfunction and optionally by the death of neuron cells. As examples of neurodegenerative diseases, mention can be made of HIV-associated dementia, multiple sclerosis, Alzheimer's disease, Parkinson's disease, amyotrophic lateral sclerosis and Pick's disease.

According to one preferred embodiment, the present invention concerns the compounds of formula (I) mentioned above for use thereof in the treatment of Alzheimer's disease.

According to one embodiment, in above-mentioned formula (I), at least one of the groups $R_1$, $R_2$, $R_3$, $R_4$ and $R_5$ differs from H.

Preferably, in above-mentioned formula (I), at least one of the groups $R_1$, $R_2$, $R_3$ and $R_4$ differs from H.

According to one embodiment, in above-mentioned formula (I), three, even four among the groups $R_1$, $R_2$, $R_3$ and $R_4$, differ from H.

According to one preferred embodiment, in formula (I), R' is H.

According to one embodiment, in formula (I) such as defined above $R_5$ is H.

Among the preferred compounds of the invention, mention can be made of those meeting formula (I) where R'=H and $R_5$=H.

Therefore, one family of preferred compounds used in the invention is composed of the compounds of following formula (II):

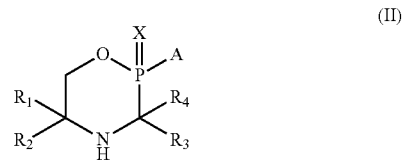

(II)

A, X, $R_1$, $R_2$, $R_3$ and $R_4$ being such as defined above in formula (I).

The compounds of formula (II) correspond to compounds of formula (I) in which R'=$R_5$=H.

According to one embodiment, in formula (I) such as defined above, $R_1$, $R_2$, $R_3$ and $R_4$, the same or different, are $(C_1-C_6)$alkyl groups.

Preferably, in formula (I) such as defined above, $R_1$, $R_2$, $R_3$ and $R_4$, the same or different, are $(C_1-C_6)$alkyl groups and $R_5$ is H.

Therefore, one family of preferred compounds used in the invention is composed of the compounds of following formula (II-1):

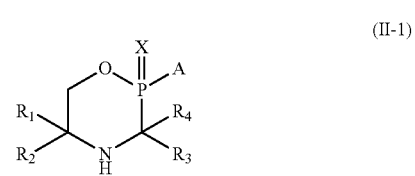

(II-1)

A and X being such as defined above in formula (I), and $R_1$, $R_2$, $R_3$ and $R_4$ being $(C_1-C_6)$alkyl groups.

The compounds of formula (II-1) correspond to compounds of formula (I) in which R'=$R_5$=H and $R_1$, $R_2$, $R_3$ and $R_4$ are selected from among $(C_1-C_6)$alkyl groups.

According to one embodiment, the groups $R_1$, $R_2$, $R_3$ and $R_4$ are methyl groups.

Among the preferred compounds used in the invention, mention can be made of the formula (I) compounds in which X is O.

Mention can also be made of the compounds of above-mentioned formulas (II) and (II-1) in which X=O.

According to one preferred embodiment, the compounds for use in the invention meet following formula (III):

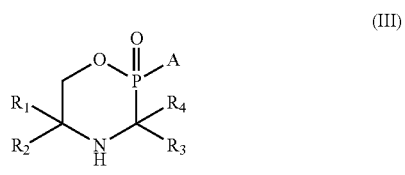

(III)

A, $R_1$, $R_2$, $R_3$ and $R_4$ being such as defined in formula (I).

Preferably, in above-mentioned formula (III), $R_1$, $R_2$, $R_3$ and $R_4$ are $(C_1-C_6)$alkyl groups and methyl groups in particular.

Preferably, in formula (I) such as defined above, A is selected from among the aryl and heteroaryl groups such as defined above.

One sub-family of compounds used in the invention is therefore composed of compounds of formula (I) such as defined above in which A is selected from the group formed by $(C_6-C_{10})$aryl groups and heteroaryl groups having 5 to 10 atoms. es Another sub-family of compounds used in the invention is therefore composed of compounds of formula (II) such as defined above, in which A is selected from the group formed by ($C_6$-$C_{10}$)aryl groups and heteroaryl groups having 5 to 10 atoms.

Another sub-family of compounds used in the invention is therefore composed of compounds of formula (II-1) such as defined above, in which A is selected from the group formed by ($C_6$-$C_{10}$)aryl groups and heteroaryl groups having 5 to 10 atoms.

Another sub-family of compounds used in the invention is therefore composed of compounds of formula (III) such as defined above. in which A is selected from the group formed by ($C_6$-$C_{10}$)aryl groups and heteroaryl groups having 5 to 10 atoms.

According to one embodiment, in above-mentioned formulas (I), (II), (II-1) and (III), A is an aryl group and preferably an optionally substituted phenyl group.

According to one embodiment, A is a non-substituted phenyl group or a phenyl group substituted by at least one substituent selected from the group formed by halogen atoms, $OR_a$, $SR_a$, $NO_2$, $NR_aR_b$, $N(R_a)COOR_c$, $R'_a$ and $OR'_a$; $R_a$, $R_b$, $R'_a$ and $R_c$ being such as defined above.

According to one embodiment, A is a phenyl group substituted by at least one substituent selected from the group formed by halogen atoms, in particular Cl or F, by $NO_2$, $NR_aR_b$ and $N(R_a)COOR_c$; $R_a$, $R_b$ and $R_c$ being such as defined above.

According to one embodiment, in above-mentioned formulas (I), (II), (II-1) and (III), A is a heteroaryl group such as defined above and optionally substituted.

Preferably, A is a heteroaryl group having 6 atoms at least one of which is a nitrogen atom. In particular, A can be selected from among the pyridinyl and pyrimidinyl groups.

According to one embodiment, in above-mentioned formulas (I), (II), (II-1) and (III), A is selected from the group formed by the 2-pyridinyl, 3-pyridinyl, 4-pyridinyl, 2-pyrimidinyl and 5-pyrimidinyl groups.

Among the compounds used in the invention, mention can also be made of the compounds of formula (I-1), (I-2) and (I-3) such as defined below.

The invention also concerns sub-families of compounds among the compounds of formula (I). Therefore, the present invention also concerns a compound of following formula (I-1):

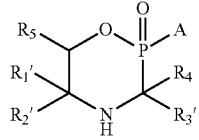

(I-1)

where:
$R'_1$, $R'_2$ and $R'_3$, the same or different, are ($C_1$-$C_6$)alkyl groups or ($C_6$-$C_{10}$)aryl groups, $R'_1$, $R'_2$ and $R'_3$ preferably being methyl groups.
$R_4$ and $R_5$, the same or different, are selected from the group formed by:
H,
($C_1$-$C_6$)alkyl groups,
($C_6$-$C_{10}$)aryl groups,
$R'_1$ and $R'_2$, together with their carrier carbon atom, able to form a spiran ring having 3 to 6 carbon atoms, or $R'_3$ and $R_4$, together with their carrier carbon atom, able to form a spiran ring having 3 to 6 carbon atoms,
A is selected from the group formed by:
($C_6$-$C_{10}$)aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, $OR_a$, $SR_a$, $NO_2$, $NR_aR_b$, $N(R_a)COOR_c$, $R'_a$ and $OR'_a$;
$R_a$ and $R_b$, the same or different, being H or ($C_1$-$C_6$)alkyl group;
$R_C$ being a —($C_1$-$C_6$)alkylene-($C_6$-$C_{10}$)aryl radical, in particular a —$CH_2$—($C_6$-$C_{10}$)aryl radical;
$R'_a$ being selected from among the groups $CF_3$, $CHF_2$ and $CH_2F$;
and when $R'_1$=$R'_2$=$R'_3$=Me, $R_4$=Me or H and $R_5$=H, A differs from the following groups:

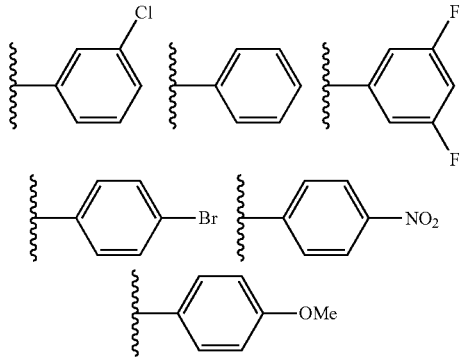

The compounds of formula (I-1) form a sub-family of formula (I) compounds in which X=O and R'=H.

Preferably, in formula (I-1), $R_5$ is H.

According to one embodiment, in formula (I-1) such as defined above, $R'_1$, $R'_2$, $R'_3$ and $R_4$, the same or different are ($C_1$-$C_6$)alkyl groups, preferably methyl.

Preferably, in formula (I-1) such as defined above, A is selected from among the aryl and heteroaryl groups such as defined above.

One sub-family of compounds of the invention is therefore composed of compounds of formula (I-1) such as defined above in which A is selected from the group formed by ($C_6$-$C_{10}$)aryl groups and heteroaryl groups having 5 to 10 atoms.

According to one embodiment, in above-mentioned formula (I-1) A is an aryl group and preferably an optionally substituted phenyl group.

According to one embodiment, A is a non-substituted phenyl group or a phenyl group substituted by at least one substituent selected from the group formed by halogen atoms, $OR_a$, $SR_a$, $NO_2$, $NR_aR_b$, $N(R_a)COOR_c$, $R'_a$ and $OR'_a$; $R_a$, $R_b$, $R'_a$ and $R_c$ being such as defined above.

According to one embodiment, A is a phenyl group substituted by at least one substituent selected from the group formed by halogen atoms, in particular Cl or F, by $NO_2$, $NR_aR_b$ and $N(R_a)COOR_c$; $R_a$, $R_b$ and $R_c$ being such as defined above.

Preferably, in formula (I-1), A is selected from among the following groups:

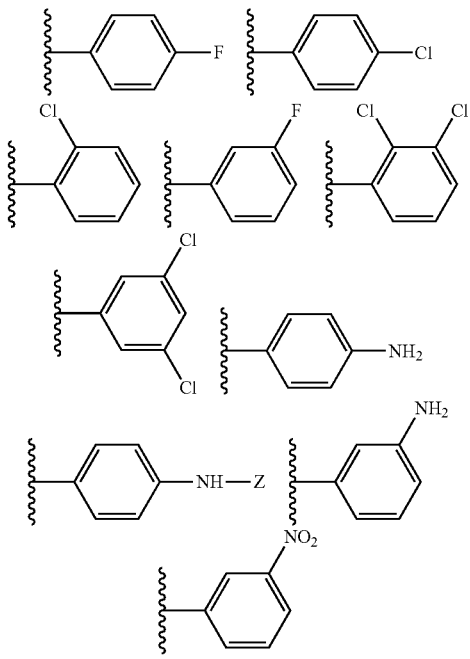

According to one embodiment, in above-mentioned formula (I-1), A is a heteroaryl group such as defined above, optionally substituted.

Preferably, in formula (I-1), A is a heteroaryl group having 6 atoms at least one of which is a nitrogen atom. In particular, A can be selected from among the pyridinyl and pyrimidinyl groups.

According to one embodiment, in formula (I-1), A is selected from the group formed by the 2-pyridinyl, 3-pyridinyl, 4-pyridinyl, 2-pyrimidinyl and 5-pyrimidinyl groups.

The present invention also concerns a compound of following formula (I-2):

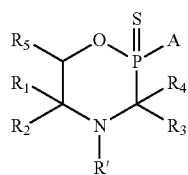

(I-2)

where:
A is selected from the group formed by:
(C$_6$-C$_{10}$)aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, OR$_a$, SR$_a$, NO$_2$, NR$_a$R$_b$, N(R$_a$)COOR$_c$, R'$_a$ and OR'$_a$;
R$_a$ and R$_b$, the same or different, being H or (C$_1$-C$_6$)alkyl group;
R$_C$ being a —(C$_1$-C$_6$)alkylene-(C$_6$-C$_{10}$)aryl radical, in particular a —CH$_2$—(C$_6$-C$_{10}$)aryl radical;
R'$_a$ being selected from among the groups CF$_3$, CHF$_2$ and CH$_2$F;
R' is H or (C$_1$-C$_6$)alkyl group;
R$_1$, R$_2$, R$_3$, R$_4$ and R$_5$, the same or different, are selected from the group formed by:
H,
(C$_1$-C$_6$)alkyl groups,
(C$_6$-C$_{10}$)aryl groups,
R$_1$ and R$_2$, together with their carrier carbon atom, able to form a spiran ring having 3 to 6 carbon atoms, and/or
R$_3$ and R$_4$, together with their carrier carbon atom, able to form a spiran ring having 3 to 6 carbon atoms.

Preferably, in formula (I-2), R'=H. Preferably, in formula (I-2), R$_5$ is H and R$_1$, R$_2$, R$_3$, and R$_4$ are alkyl groups, methyl in particular.

Preferably, in formula (I-2), A is a phenyl group, optionally substituted, in particular by at least one halogen atom.

The present invention also concerns a compound of following formula (I-3):

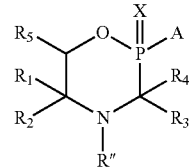

(I-3)

where:
X is O or S;
A is selected from the group formed by:
(C$_6$-C$_{10}$)aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, OR$_a$, SR$_a$, NO$_2$, NR$_a$R$_b$, N(R$_a$)COOR$_c$, R'$_a$ and OR'$_a$;
R$_a$ and R$_b$, the same or different, being H or (C$_1$-C$_6$)alkyl group;
R$_C$ being a —(C$_1$-C$_6$)alkylene-(C$_6$-C$_{10}$)aryl radical, in particular a —CH$_2$—(C$_6$-C$_{10}$)aryl radical;
R'$_a$ being selected from among the groups CF$_3$, CHF$_2$ and CH$_2$F;
R" is a (C$_1$-C$_6$)alkyl group;
R$_1$, R$_2$, R$_3$, R$_4$ and R$_5$, the same or different, are selected from the group formed by:
H,
(C$_1$-C$_6$)alkyl groups,
(C$_6$-C$_{10}$)aryl groups,
R$_1$ and R$_2$, together with their carrier carbon atom, able to form a spiran ring having 3 to 6 carbon atoms, and/or
R$_3$ and R$_4$, together with their carrier carbon atom, able to form a spiran ring having 3 to 6 carbon atoms.

Preferably, in formula (I-3), X=O. Preferably, in formula (I-3), R$_5$ is H and R$_1$, R$_2$, R$_3$, and R$_4$ are alkyl groups, methyl in particular.

Preferably, in formula (I-3), A is a phenyl group, optionally substituted in particular by at least one halogen atom.

Among the compounds of formula (I), (I-1), (I-2) or (I-3), particular mention can be made of the following compounds:

| | |
|---|---|
| 3b 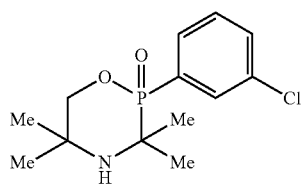 | 3i 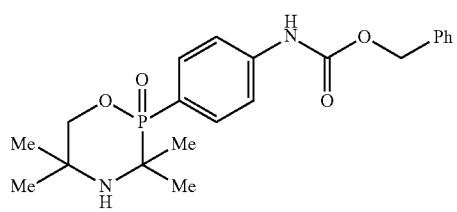 |
| 3a 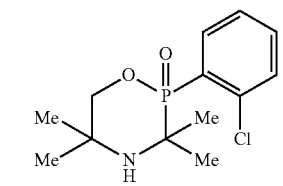 | 3j 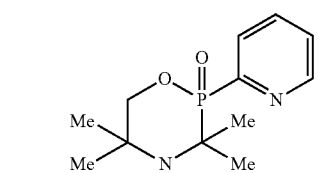 |
| 3c 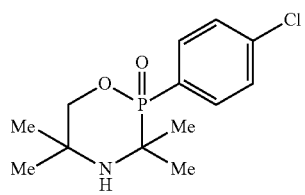 | 3k 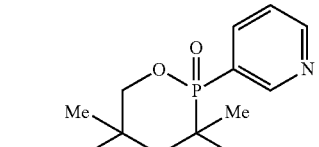 |
| 3d 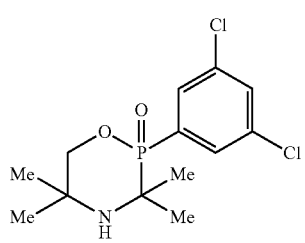 | 3l 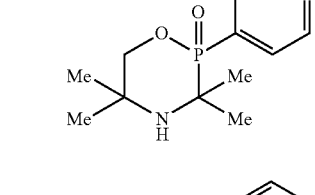 |
| 3e 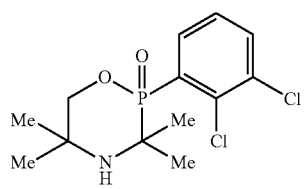 | 3m 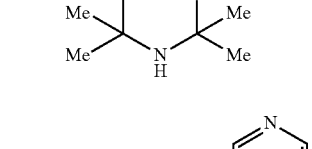 |
| 3f 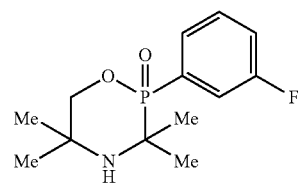 | 3n 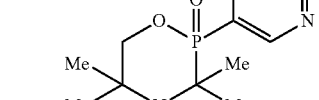 |
| 3g 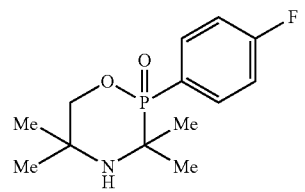 | 6 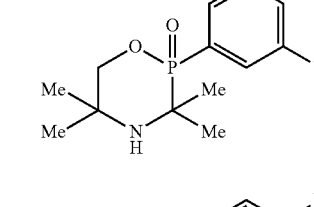 |
| 3h 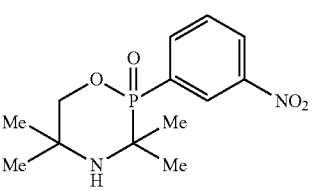 | 7 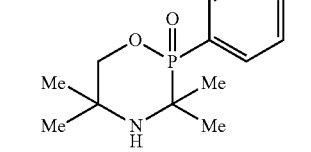 |

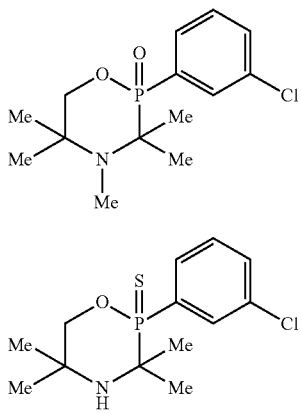

The compounds of the invention have neuroprotective action. The compounds of the invention can therefore be used to prepare medicinal products.

The invention therefore also concerns medicinal products which comprise a compound of formula (I-1), (I-2) or (I-3), or an addition salt thereof with a pharmaceutically acceptable acid.

These medicinal products find therapeutic application in particular for the treatment of neurodegenerative diseases.

The present invention also concerns a pharmaceutical composition comprising at least one compound of formula (I-1), (I-2) or (I-3) such as defined above, in association with at least one pharmaceutically acceptable vehicle or excipient.

The present invention therefore also concerns pharmaceutical compositions comprising a compound of the invention as active ingredient, namely a compound meeting one of formulas (I-1), (I-2) or (I-3). These pharmaceutical compositions contain an effective dose of at least one compound of the invention, or a pharmaceutically acceptable salt, and at least one pharmaceutically acceptable excipient.

Said excipients are selected in accordance with the desired pharmaceutical form and administration mode, from among usual excipients known to persons skilled in the art.

In the pharmaceutical compositions of the present invention for oral, sublingual, sub-cutaneous, intramuscular, intravenous, topical, local, intratracheal, intranasal, transdermal or rectal administration, the active ingredient of above formula (I-1), (I-2) or (I-3), or salt thereof, can be administered in unit administration form in a mixture with conventional pharmaceutical excipients, to animals and to human beings to treat the above disorders or diseases.

Suitable unit administration forms comprise the forms via oral route such as tablets, hard or soft capsules, powders, granules and oral solutions or suspensions, sublingual, buccal, intratracheal, intraocular, intranasal, inhalation administration forms, topical, transdermal, sub-cutaneous, intramuscular or intravenous administration forms, rectal administration forms and implants. For topical application, the compounds of the invention can be used in creams, gels, ointments or lotions.

The present invention concerns a compound of formula (I-1), (I-2) or (I-3) such as defined above, or an addition salt of this compound with a pharmaceutically acceptable acid, for use thereof as medicinal product.

In another aspect, the present invention also concerns a method for treating the above-mentioned neurodegenerative diseases, which comprises the administering to a patient of an effective dose of a compound of the invention, or one of the pharmaceutically acceptable salts thereof.

FIGURES

FIG. 1: Behavioural effects induced by compound 3b in mice treated with $A\beta_{25-35}$: (a, b) spontaneous alternation in Y-maze, (c) passive avoidance test and (d, e) object recognition test. The animals were treated with compound 3b (0.3-3 mg/kg IP) 20 min before the $A\beta_{25-35}$ or Sc.Aβ peptide (9 nmol ICV). After 7 days, the mice were tested in the Y-maze: (a) spontaneous alternation performance and (b) total number of arm entries; followed by passive avoidance test: (c) step-through latency; then object recognition test: analysis of preference for object 2 (novel at session 3) computed from (d) the number of contacts with the objects and (e) contact time. ANOVA: $F_{(6,167)}$=4.58, $p<0.001$ at (a); $F_{(6,167)}$=2.65, $p<0.05$ at (b); H=20.5, $p<0.01$ at (c), n=18-30 per group. **$p<0.01$ compared with the (Sc.Aβ+V) group; #$p<0.05$, ##$p<0.01$ compared with the ($A\beta_{25-35}$+V) group; Dunnett test at (a) and Dunn test at (c). ° $p<0.05$, °° $p<0.01$, °°° $p<0.001$ compared with chance level (50 s); t-test, n=4-13 at (d, e).

Figure 2:
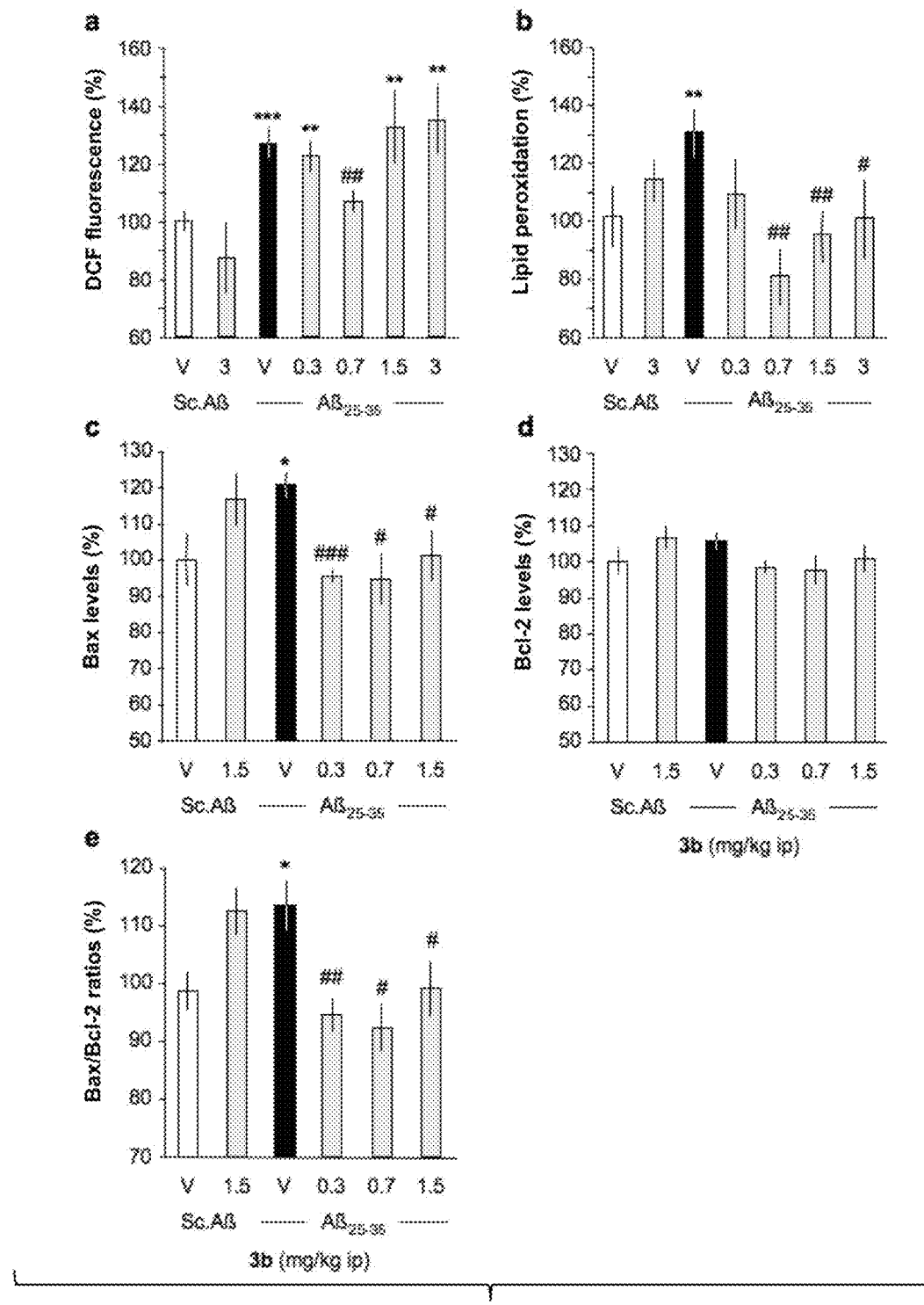

FIG. 2: Neuroprotective effect of compound 3b in mice treated with $A\beta_{25-35}$: (a) Level of reactive oxygen species in hippocampus, (b) Level of lipid peroxidation in frontal cortex, (c) Level of Bax protein in hippocampus, (d) Level of Bcl-2 and (e) Bax/Bcl-2 ratio. The mice were treated with compound 3b (0.3-3 mg/kg IP) 20 min before the $A\beta_{25-35}$ or Sc.Aβ peptide (9 nmol ICV) and sacrificed after 9 days. Values are expressed as % of the control group (Sc.Aβ+V). ANOVA: $F_{(6,47)}$=2.60, $p<0.05$, n=6-12 per group at (a); $F_{(6,62)}$=5.03, $p<0.001$, n=7-13 at (b); $F_{(5,36)}$=3.36, $p<0.05$ at (c); F<1 at (d); $F_{(5,36)}$=3.72, $p<0.01$, n=5-6 at (e). *$p<0.05$, $p<0.01$, * $p<0.001$ compared with group (Sc.Aβ+V); #$p<0.05$, ##$p<0.01$, ###$p<0.001$ compared with group ($A\beta_{25-35}$+V); Dunnett test.

Figure 3:
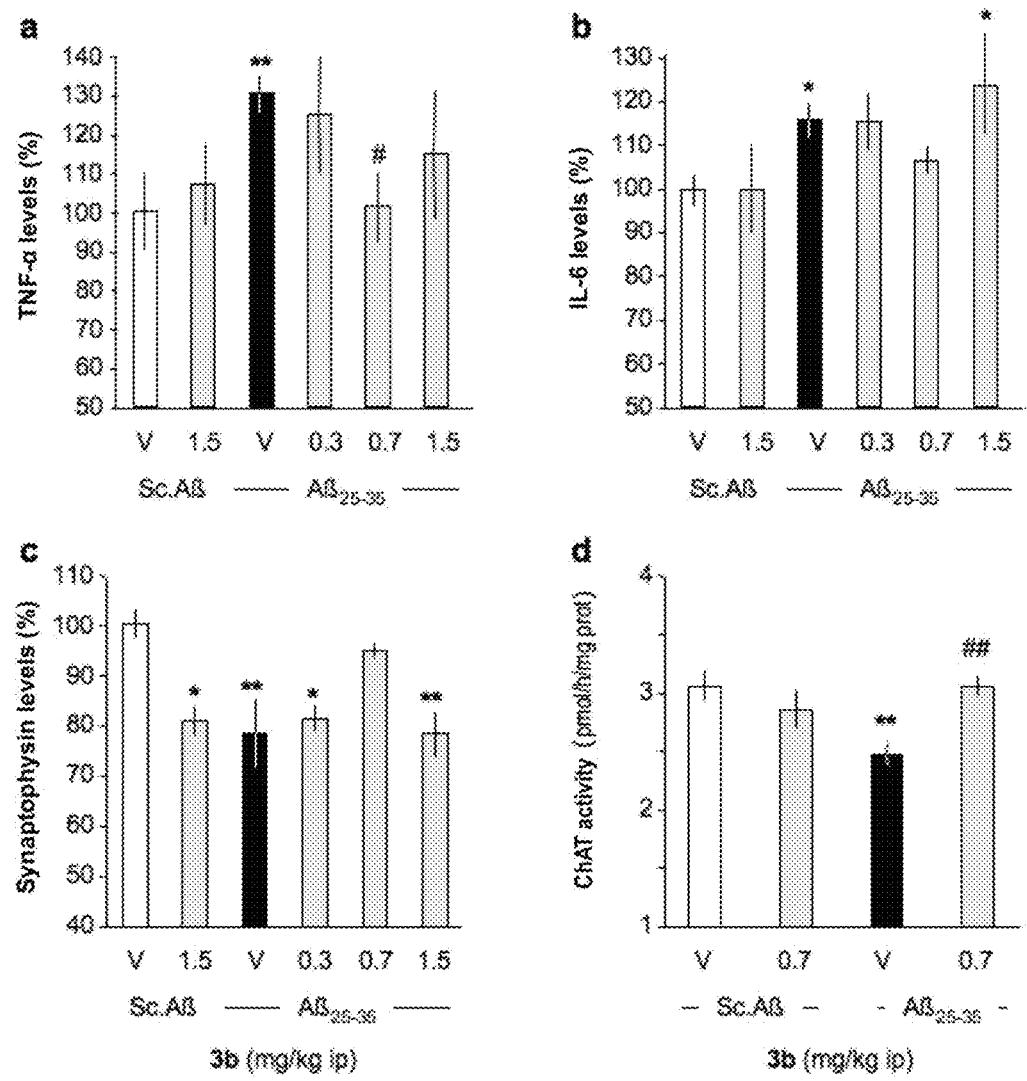

FIG. 3: Neuroprotective effect of compound 3b in the hippocampus of mice treated with $A\beta_{25-35}$: (a) TNFα level, (b) IL1β level (c) synaptophysin levels (c) and ChAT activity (d). The mice were treated with the 3b compound (0.3-3 mg/kg IP) 20 min before peptide $A\beta_{25-35}$ or Sc.Aβ (9 nmol ICV) and sacrificed after 9 days. Values are expressed as % of the control group (Sc.Aβ+V). ANOVA: $F_{(5,56)}$=1.09, $p>0.05$, n=7-11 per group at (a); $F_{(5,67)}$=3.82, $p<0.01$, n=5-6 at (b); $F_{(5,30)}$=4.55, $p<0.01$ at (c); $F_{(3,23)}$=4.97, $p<0.01$ at (d). *$p<0.05$, **$p<0.01$ compared with the group (Sc.Aβ+V); #$p<0.05$, ##$p<0.01$ compared with group ($A\beta_{25-35}$+V); Dunnett test.

Figure 4:
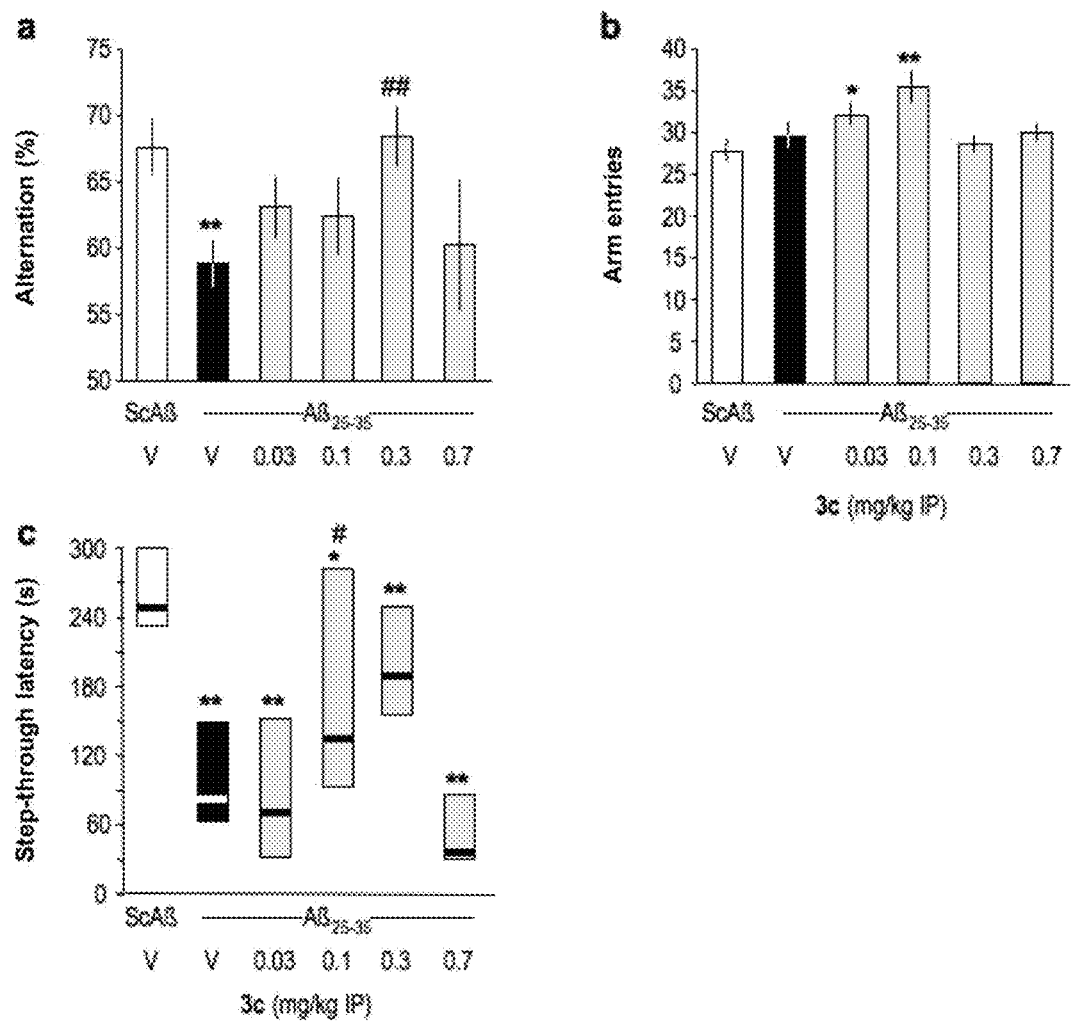

FIG. 4: Effects of compound 3c in mice treated with the peptide $A\beta_{25-35}$: (a, b) spontaneous alternation in Y-maze, and (c) passive avoidance. The mice were treated with compound 3c (0.03-0.7 mg/kg IP) 20 min before peptide $A\beta_{25-35}$ or Sc.Aβ (9 nmol ICV). After 7 days the mice were tested in the Y-maze: (a) spontaneous alternation performance and (b) total number of arm entries; then passive avoidance test: (c) step-through latency. ANOVA: $F_{(5,67)}$=2.54, $p<0.05$ at (a); $F_{(5,67)}$=3.80, $p<0.01$ at (b); H=21.4, $p<0.001$ at (c), n=4-14 per group. *$p<0.05$, **$p<0.01$ compared with group (Sc.Aβ+V); #$p<0.05$, ##$p<0.01$ compared with group ($A\beta_{25-35}$+V); Dunnett test at (a,b) and Dunn at (c).

Figure 5:
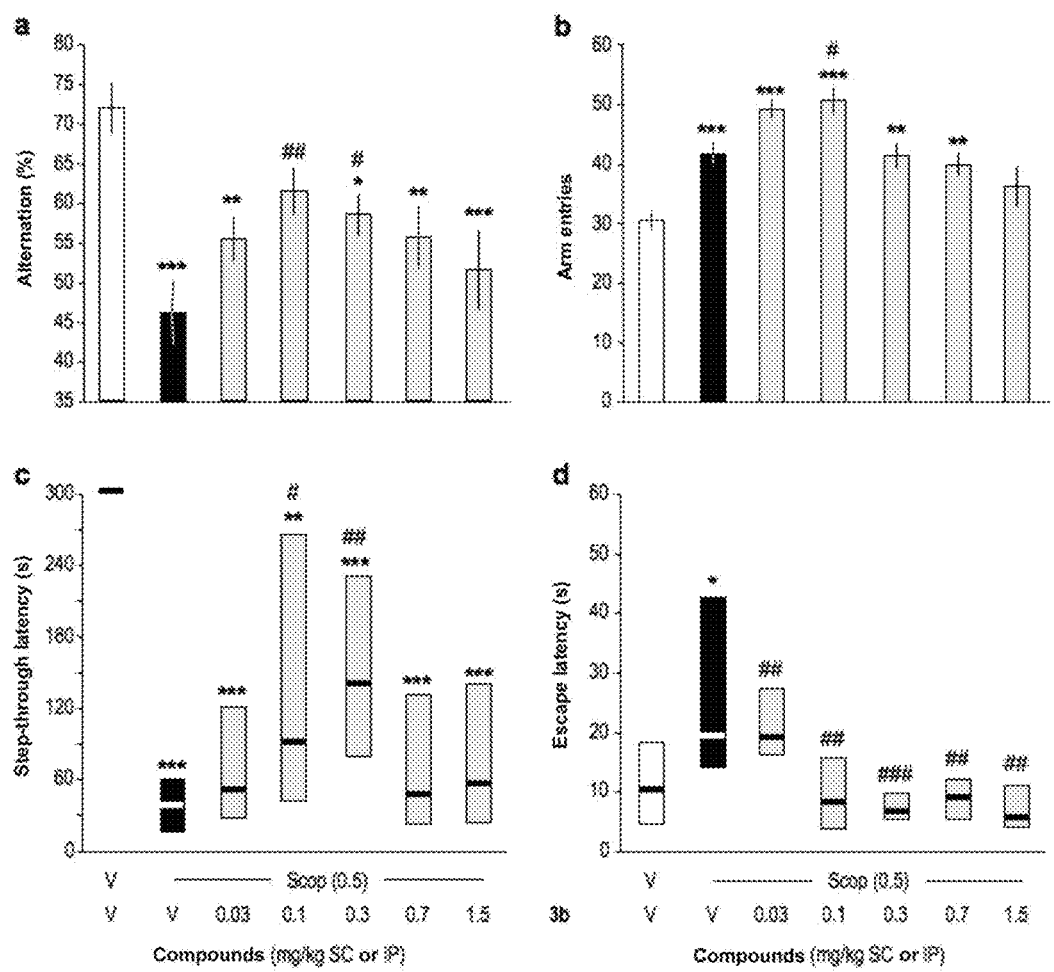

FIG. 5: Anti-amnesic effect of compound 3b in mice treated with scopolamine: (a, b) spontaneous alternation in Y-maze, and (c, d) passive avoidance. The mice were given compound 3b (0.03-1.5 mg/kg IP) 10 min before scopolamine (0.5 mg/kg SC), 20 min before the Y-maze session or passive avoidance training. Y-maze test: (a) spontaneous alternation and (b) total number of arm entries; retention of passive avoidance: (c) step-through latency and (d) escape latency. ANOVA: $F_{(6,94)}=5.32$, $p<0.0001$ at (a); $F_{(6,94)}=10.6$, $p<0.0001$ at (b); H=31.4, $p<0.0001$ at (c); H=24.3, $p<0.001$ at (d); n=12-19 per group. *$p<0.05$, $p<0.01$, *$p<0.001$ compared with group (Sc.Aβ+V); #$p<0.05$, ##$p<0.01$, ###$p<0.001$ compared with group (Aβ25-35+V); Dunnett test at (a, b) and Dunn at (c, d).

Figure 6:
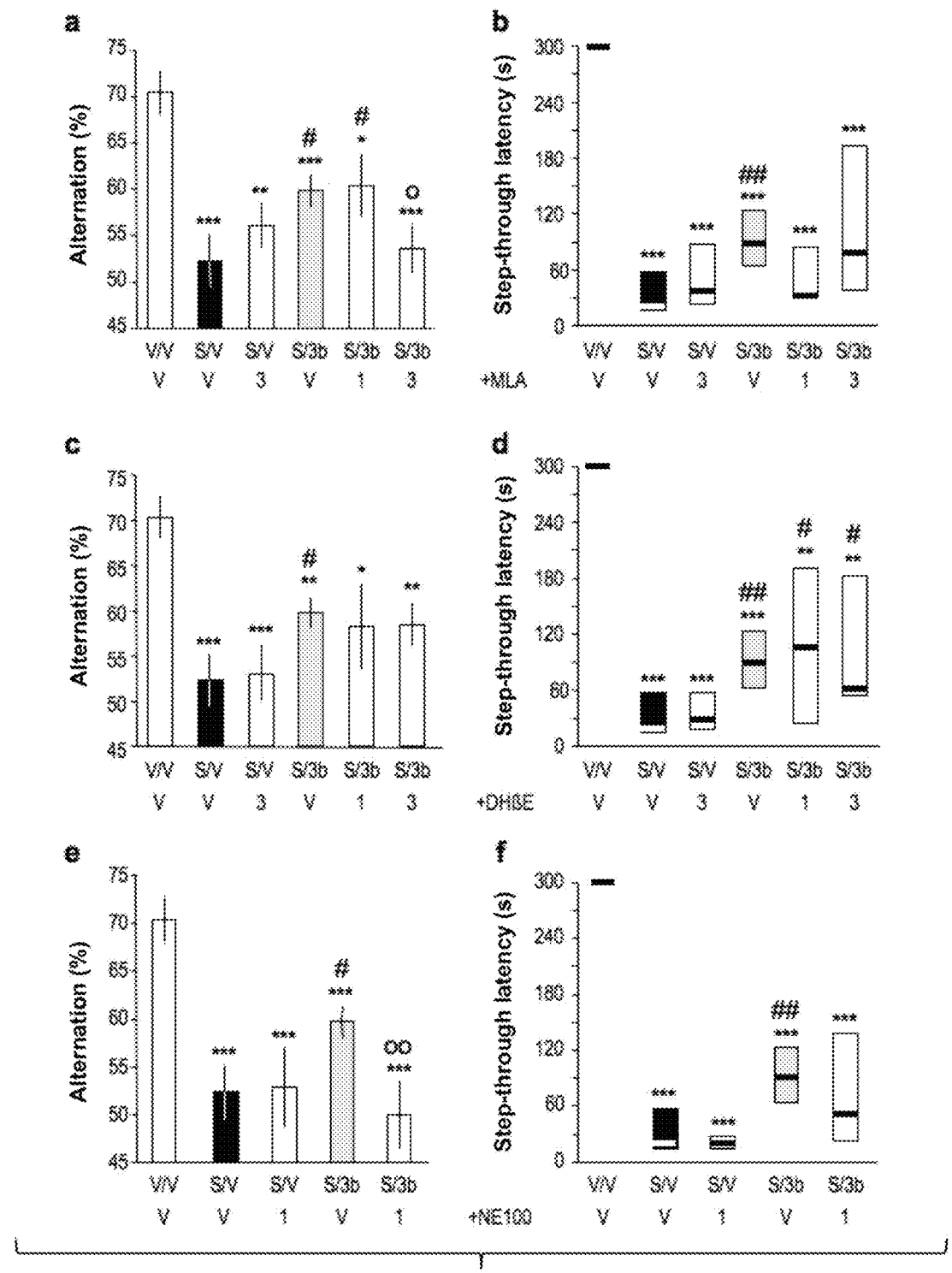

FIG. 6: Analysis of the antagonism of anti-amnesic effects of compound 3b in mice treated with scopolamine: (a, c, e) spontaneous alternation in Y-maze, and (b, d, f) step-through latency at recall session of passive avoidance. The mice were treated with methyllycaconitine (MLA, 1 or 3 mg/kg IP), dihydro-ß-erythroidine (DHßE, 1 or 3 mg/kg IP), or NE100 (1 mg/kg IP), simultaneously with compound 3b (0.1 mg/kg IP) 10 min before scopolamine (S, 0.5 mg/kg SC), 20 min before behavioural session. ANOVA: $F_{(5,87)}=7.19$, $p<0.0001$ at (a); H=31.3, $p<0.0001$ at (b); $F_{(5,82)}=5.82$, $p<0.0001$ at (c); H=28.8, $p<0.0001$ at (d); $F_{(4,77)}=10.0$, $p<0.0001$ at (e); H=30.5, $p<0.0001$ at (f); n=12-17 per group. *$p<0.05$, $p<0.01$, *$p<0.001$ compared with group (Sc.Aβ+V); #$p<0.05$, ##$p<0.01$, ###$p<0.001$ compared with group (Aβ$_{25-35}$+V); Dunnett test at (a, b) and Dunn at (c, d).

Figure 7:
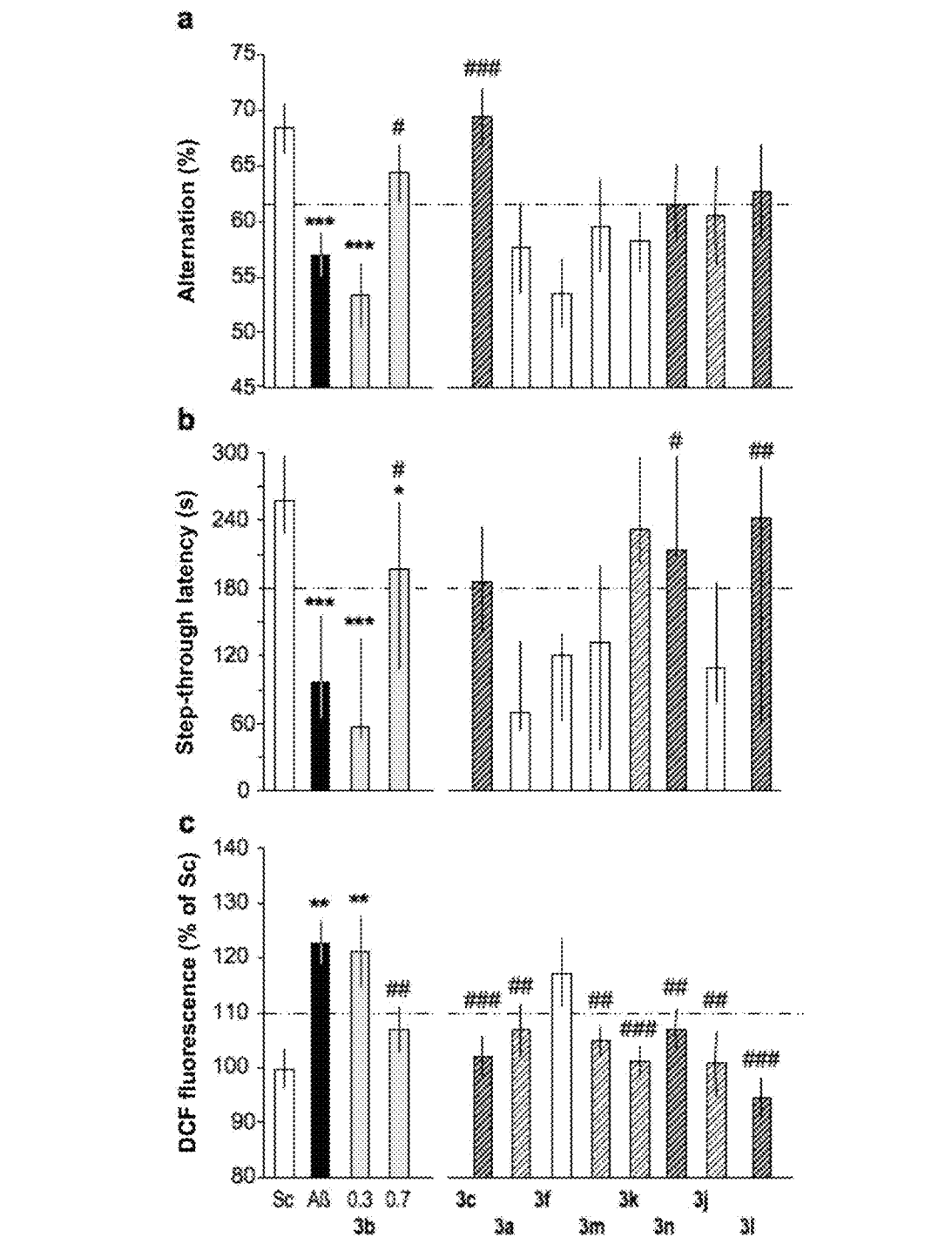

FIG. 7: Screening of phosphinolactones as neuroprotectors in mice treated with peptide Aβ$_{25-35}$: (a) spontaneous alternation; (b) passive avoidance step-through latency; (c) Levels of reactive oxygen species in hippocampus. The mice were given compound 3b (0.3, 0.7 mg/kg IP) or a dose of each compound (0.3 mg/kg IP) 20 min before I'Aβ$_{25-35}$ or the control peptide Sc.Aβ (9 nmol ICV). The animals were tested in the Y-maze on Day 7 after the ICV injections and for passive avoidance on Days 8-9, and then sacrificed. In each graph at (a-c), the 50% protection level compared with the deficit induced by Aβ$_{25-35}$ is plotted as a dotted line. It is to be noted that at (a), the column represents the median and the error bars represent the deviations 25%-75% (=asymmetric deviations). n=12 at (a, b) and 5-6 at (c). ANOVA on groups 1-4: $F_{(3,63)}=7.95$, $p<0.001$ at (b); H=24.1, $p<0.0001$ at (c); $F_{(3,44)}=6.33$, $p<0.01$ at (d). *$p<0.05$, $p<0.01$, *$p<0.001$ compared with group (Sc.Aβ+V); #$p<0.05$, ##$p<0.01$, ###$p<0.001$ compared with group (Aβ$_{25-35}$+V); Dunnett test at (a, c) and Dunn at (b). The values of the groups 5-12 (screened compounds) were analysed by t-test at (a, c) or Mann-Whitney at (b).

Figure 8:
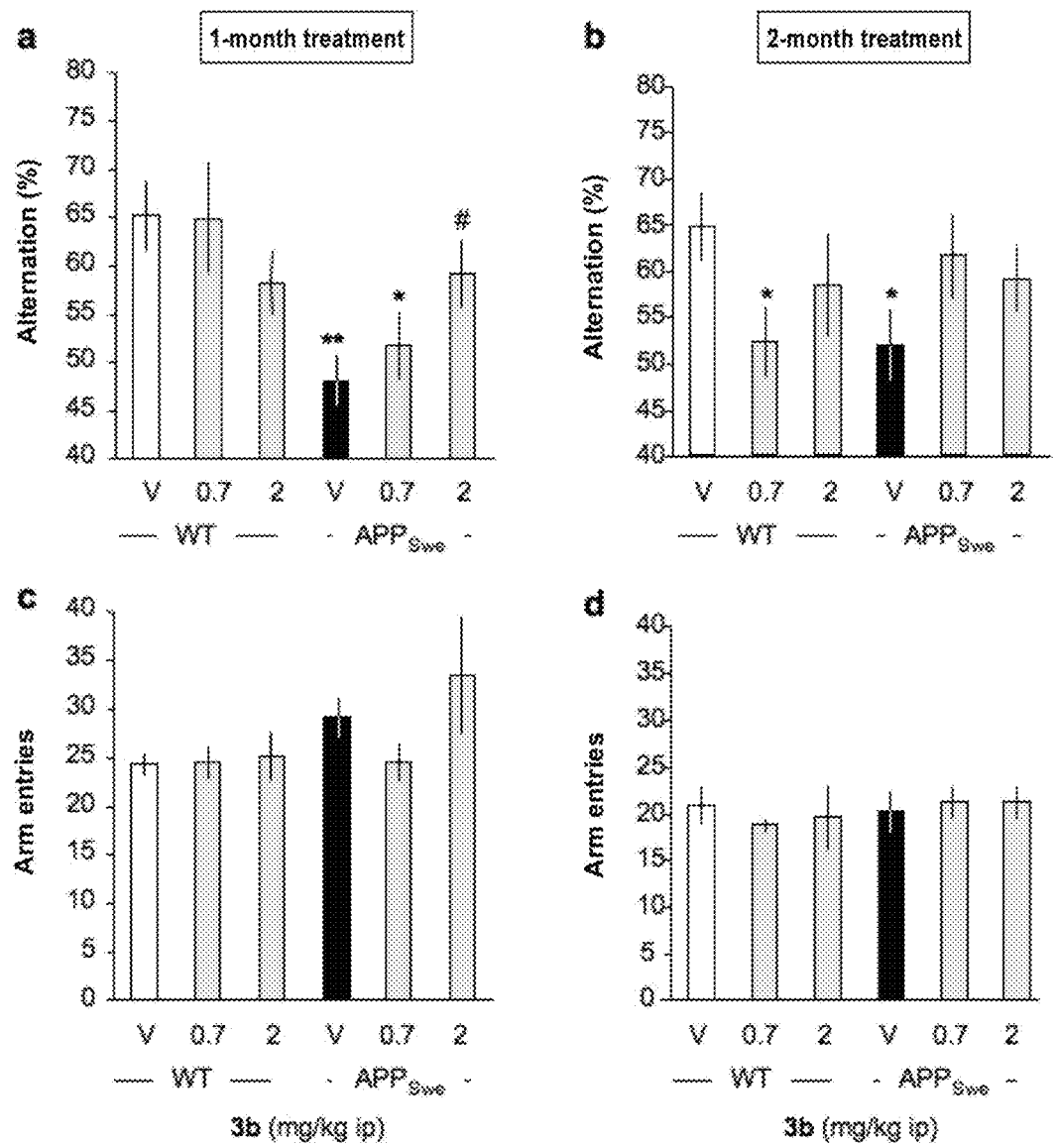

FIG. 8: Spontaneous alternation (a, b) and total number of arm entries (c, d) of APP$_{Swe}$ mice given compound 3b, in the Y-maze, after treatment of one month (a, c) and 2 months (b, d). The animals were given compound 3b (0.7 or 2 mg/kg IP) 3 times per week for 1 or 2 months. N=6-15 per group. ANOVA: $F_{(5,49)}=3.84$, $p<0.01$ at (a); $F_{(5,54)}=1.54$, $p>0.05$ at (b); F<1 at (c) et (d). *$p<0.05$, **$p<0.01$ compared with group (WT+V); #$p<0.05$ compared with group (APP$_{Swe}$+V); Dunnett test at (a, b).

Figure 9:
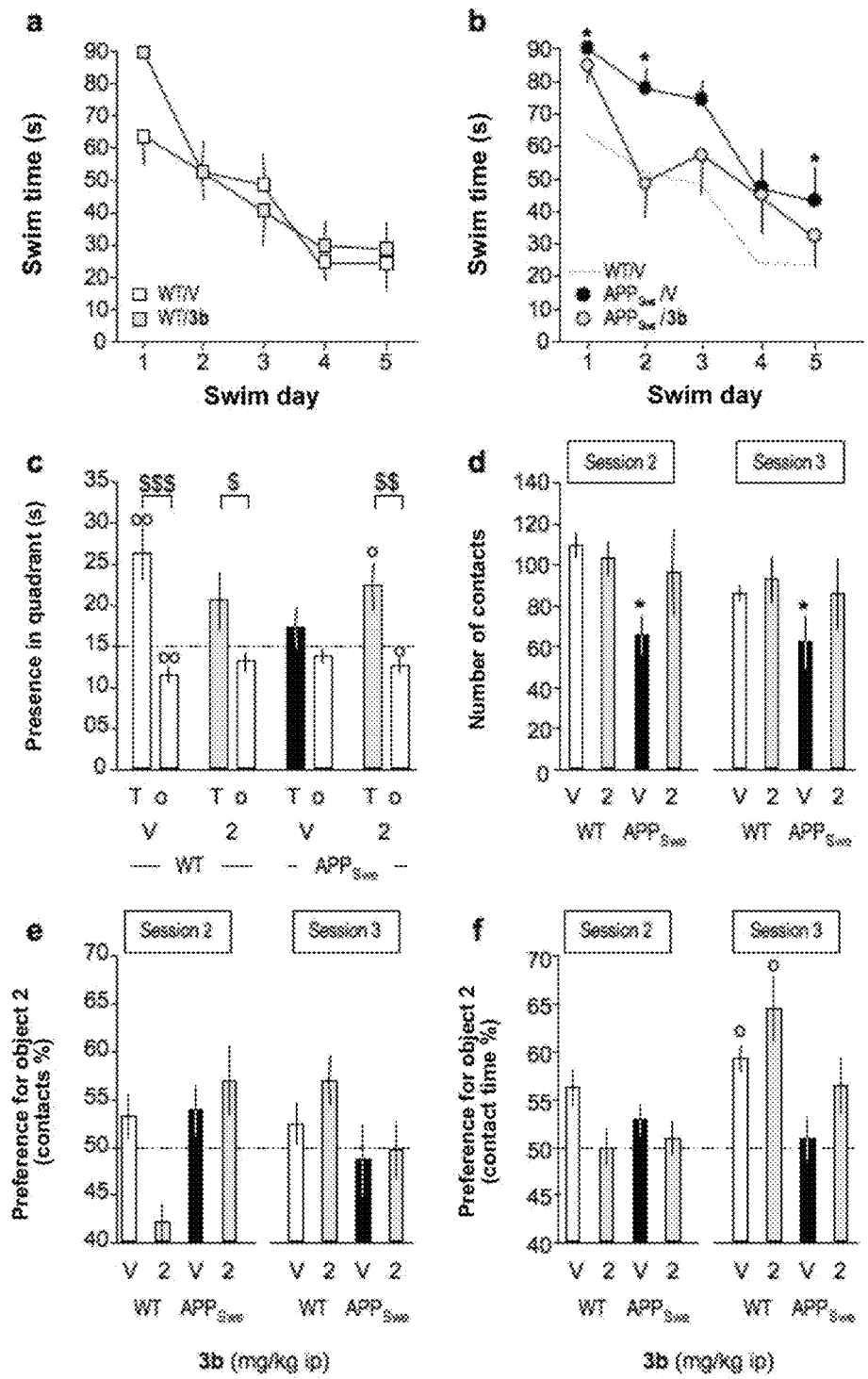

FIG. 9: Spatial learning in pool (a-c) and object recognition (d-f) for APP$_{Swe}$ mice after 2-month treatment with compound 3b. Pool: acquisition profiles of WT mice treated with V and 3b (2 mg/kg) (a) or APP$_{Swe}$ mice (b). (c) Presence in training quadrant (T) and mean in the other quadrants (o) during trial test performed 48 h after the last training session. Friedman non-parametric ANOVA with repeated measures: Fr=21.7, $p<0.001$ for the group WT/V, Fr=21.8, $p<0.001$ for the group WT/3b at (a); Fr=13.0, $p<0.05$ for group APP$_{Swe}$/V, Fr=12.2, $p<0.05$ for group APP$_{Swe}$/3b at (b). Object recognition: Number of contacts with the objects during sessions 2 and 3 (d) and preferences for object at position 2 computed as contacts (e) or contact time (f). ° $p<0.05$, °° $p<0.01$ compared with chance level: 15 s at (c), 50% at (e, f), One Sample t-test. $ $p<0.05$, $$ $p<0.01$, $$$ $p<0.001$ compared with the mean of the other quadrants (o) at (c). *$p<0.05$ compared with group WT/V at (d).

Figure 10:
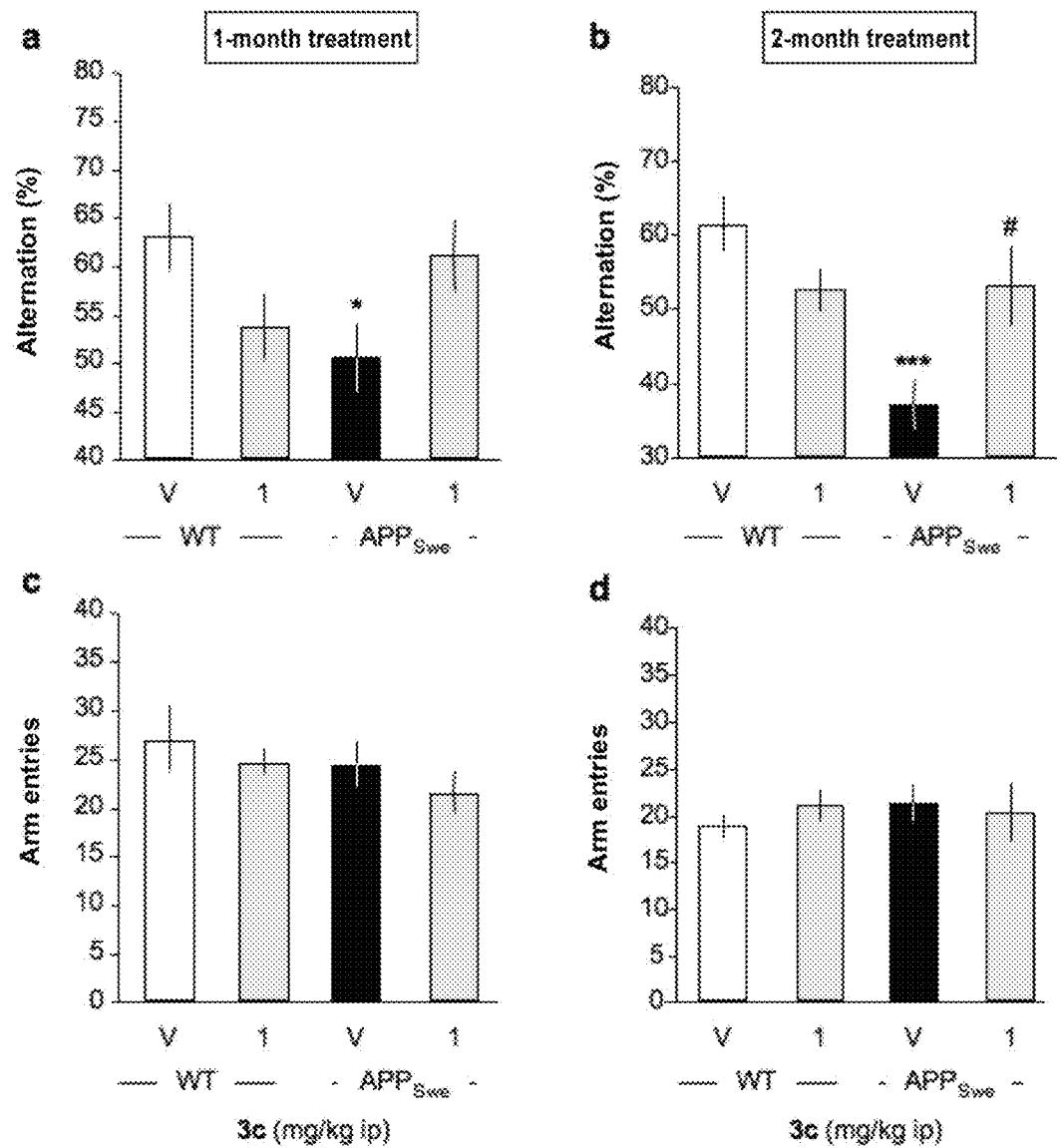

FIG. 10: Spontaneous alternation (a, b) and number of arm entries (c, d) for APP$_{Swe}$ mice treated with compound 3c, in the Y-maze, after treatment for 1 month (a, c) or 2 months (b, d). The animals were given compound 3c (1 mg/kg IP) 3 times per week for 1 or 2 months. N=10-13 per group. ANOVA: $F_{(3,45)}=3.61$, $p<0.05$ at (a); $F_{(3,38)}=6.33$, $p<0.01$ at (b); F<1 at (c) and (d). *$p<0.05$, ***$p<0.001$ compared with group WT/V; #$p<0.05$ compared with group APP$_{Swe}$/V; Dunnett test at (a, b).

Figure 11:
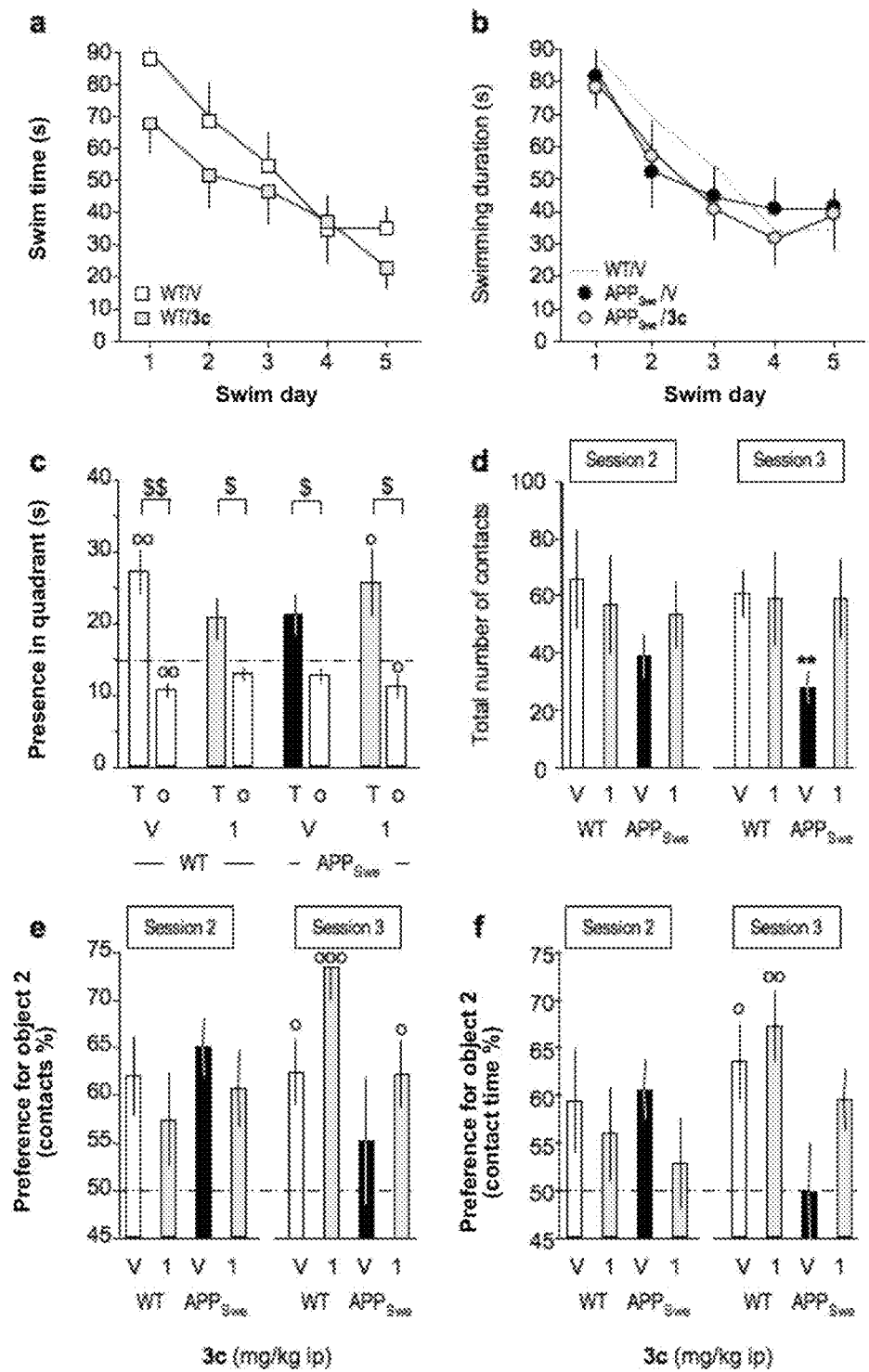

FIG. 11: Spatial learning in pool (a-c) and object recognition (d-f) for APP$_{Swe}$ mice after 2-month treatment with compound 3c. Pool: acquisition profiles of WT mice treated with V and 3c (2 mg/kg) (a) or APP$_{Swe}$ mice (b). (c) Presence in training quadrant (T) and mean in the other quadrants (o) during the trial test performed 48 h after the last training session. Friedman non-parametric ANOVA with repeated measures: Fr=20.7, $p<0.001$ for group WT/V, Fr=17.5, $p<0.001$ for group WT/3c at (a); Fr=11.4, $p<0.05$ for group APP$_{Swe}$/V, Fr=13.6, $p<0.01$ for group APP$_{Swe}$/3b at (b). Object recognition: Number of contacts with the objects during sessions 2 and 3 (d) and preferences for the object at position 2 computed as contacts (e) or contact time (f). ° $p<0.05$, °° $p<0.01$, °°° $p<0.001$ compared with chance level: 15 s at (c), 50% at (e, f), One Sample t-test. $ $p<0.05$, $$ $p<0.011$ compared with the men of the other quarters(o) at (c). *$p<0.05$ compared with group WT/V at (d).

Figure 12:
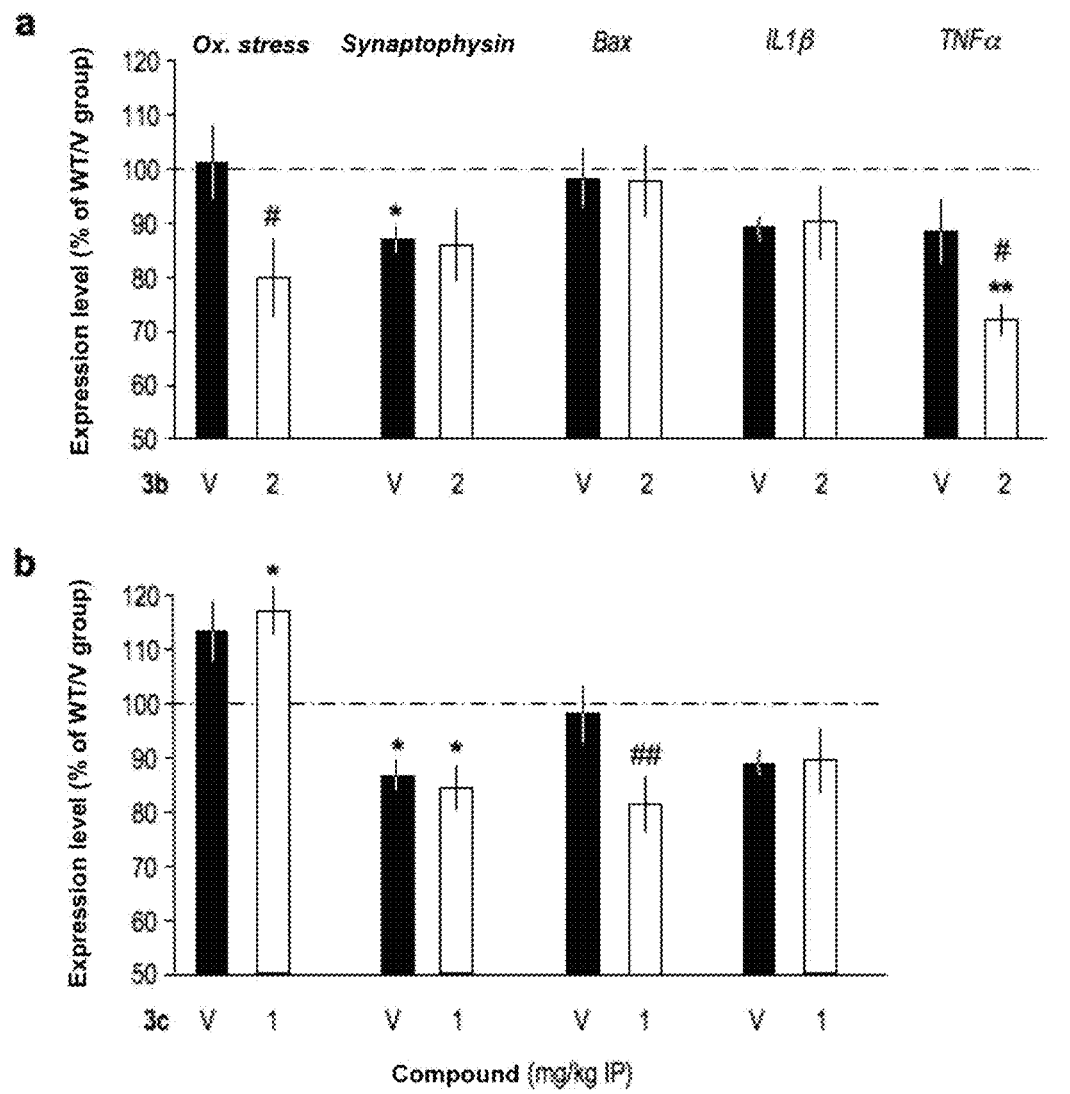

FIG. 12: Biochemical analyses of the effect of treatments with compound 3b (a) or 3c (b) in the hippocampus of APP$_{Swe}$ mice. Oxidative stress was measured via the level of peroxidation of membrane lipids at (a), or DCF fluorescence at (b). The expression levels of synaptophysin, Bax, IL1β and TNFα were measured using commercial Elisa kits. The values are given as % of the control group WT/V. N=6-8 per group. *$p<0.05$, **$p<0.01$ compared with group WT/V; #$p<0.05$, ##$p<0.01$ compared with group APP$_{Swe}$/V; Student t-test.

Figure 13:
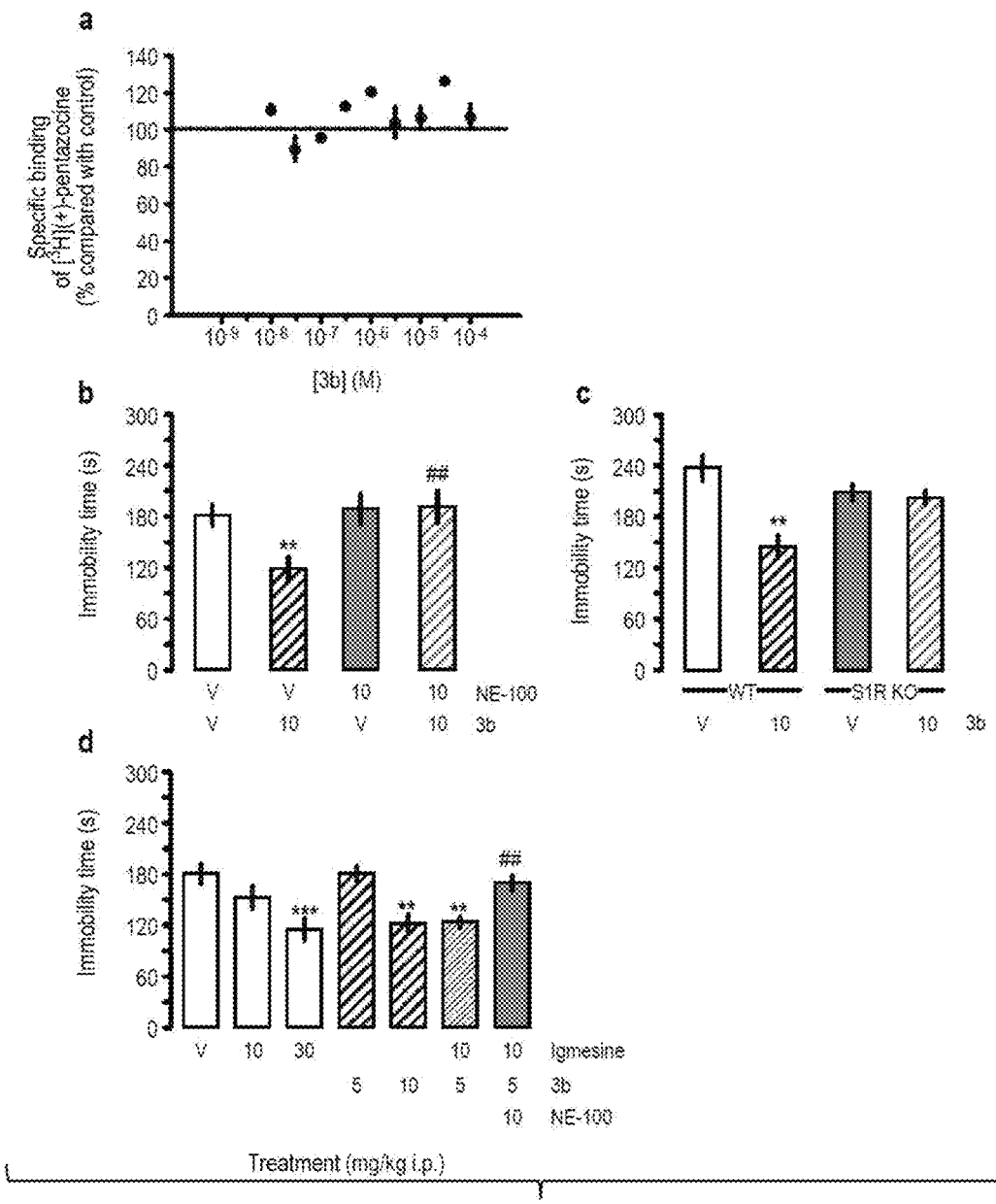

FIG. 13: Assays of compound 3b as positive modulator of the sigma-1 protein. (a) Compound 3b does not modify binding of [$^3$H](+)-pentazocine on the sigma-1 receptor, in preparations of guinea pig forebrain membranes over a concentration range of 10 nM à 100 µM. (b) The antidepressant effect of compound 3b in the forced swim test in mice is blocked by the selective antagonist NE-100. Male Swiss mice aged 7 weeks (n=10-12 per group) were forced to swim for 15 min on Day 1 and 6 min on Day 2. They were given NE-100 (10 mg/kg ip), 10 min before compound 3b (10 mg/kg ip) and 20 min before the session of Day 2. Immobility was measured over the last 5 minutes of the session. The vehicle solution was distilled water. $F_{(3,42)}=4.45$, $p<0.01$; $p<0.01$ vs. group V/V, ##$p<0.01$ vs. group V/3b, Dunnet test. (c) No antidepressant effect of compound 3b in KO mice for the sigma-1 protein (S1R KO). Wild-type mice (Wt, n=14-15) and S1R KO mice (n=9-10) were forced to swim 15 min on Day 1 and 6 min on Day 2. They were given compound 3b (10 mg/kg ip) 20 min before the session on Day 2. Immobility was measured during the last 5 minutes of the session. The vehicle solution was distilled water. $F_{(3,49)}=6.64$, $p<0.001$; $p<0.01$ vs. group Wt/V, Dunnett test. (d) Potentiation of the effects of a sigma-1 agonist by compound 3b in the forced swim test. Male Swiss mice aged 7 weeks (n=8-23 per group) were forced to swim for 15 min on Day 1 and 6 min on Day 2. They were given igmesine (10, 30 mg/kg ip) and/or compound 3b (10 mg/kg ip) 20 min before the session on Day 2. NE-100 (10 mg/kg ip) was injected 10 min before igmesine and compound 3b. Immobility was measured during the last 5 minutes of the session. The vehicle solution was distilled water. $F_{(6,90)}=5.59$, $p<0.0001$; ***$p<0.001$ vs. group V, ##$p<0.01$ vs. group V/Igmesine (10)+3B (5), Dunnett test.

The following examples describe the preparation of some compounds conforming to the invention. These examples are nonlimiting and solely illustrate the invention.

EXAMPLES

Preparation of Compounds of the Invention
General Information on the Method for Preparing Compounds of the Invention lecular Chemistry" [Volle, J.-N., Filippini, D., Krawczy, B., Kaloyanov, N., Van der Lee, A., Maurice, T., Pirat, J.-L., Virieux, D. *Org. Biomol. Chem.* 2010, 8, 1438-1444].

Scheme 2. Alternative method for preparing compounds of formula (C) from alkyl arylphosphinates and 1,3-oxazolidines of formula (A).

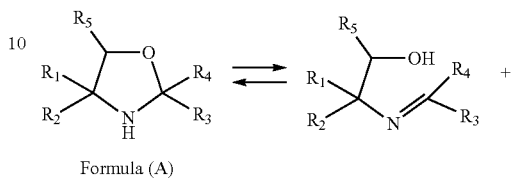

Formula (A)

Scheme 1. General method for preparing compounds of formula (B), (C), (D) and (E), from methyl hypophosphite and 1,3-oxazolidines of formula (A).

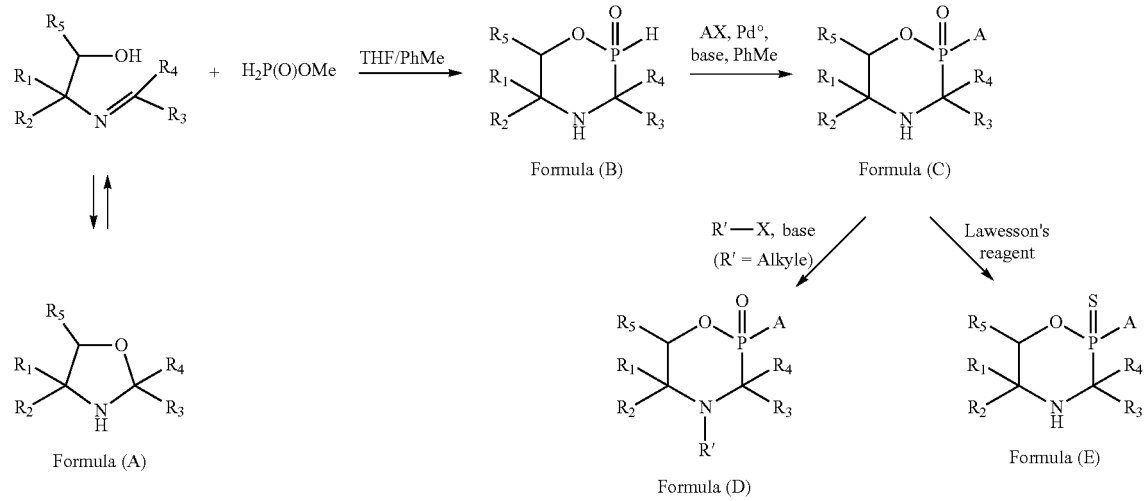

As is conventional, the structures having formula (C) can be prepared by palladium-catalysed arylation of H-1,4,2-oxazaphosphinane precursors of formula (B). The compounds of formula (B) are accessible via addition/cyclisation reaction of methyl hypophosphite [Cristau, H.-J.; Coulombeau, A.; Genevois-Borella, A.; Pirat, J.-L. *Tetrahedron Lett.* 2001, 42, 4491-4494] with iminoalcohol form of 1,3-oxazolidines of formula (A) [Volle, J.-N., Filippini, D., Krawczy, B., Kaloyanov, N., Van der Lee, A., Maurice, T., Pirat, J.-L., Virieux, D. *Org. Biomol. Chem.* 2010, 8, 1438-1444; Cristau H.-J., J. Monbrun, Monique Tillard, J.-L. Pirat, *Tetrahedron Lett.* 2003, 3183-3186; Pirat J.-L., Monbrun J., Virieux D., Cristau H.-J. *Tetrahedron* 2005, 7029-7036; Volle, J.-N., Virieux, D., Starck, M., Monbrun, J., Clarion, L., Pirat J.-L. *Tetrahedron Asymmetry* 2006, 1402-1408; and Volle, J.-N., Kaloyanov, N., Saada, M. C., Virieux, D., Pirat, J.-L. *Tetrahedron lett.* 2007, 48, 4695-4697].

Derivatives of N-alkyl type of formula (D) (R=alkyl) can be accessible via N-alkylation reaction of the corresponding secondary amine derivatives (C). Regarding the thiono derivatives (P=S, formula E), these can be obtained by treating oxo derivatives (P=O, C) with Lawesson's reagent.

An alternative route can be followed to access the compounds of formula (C). It consists of direct condensation, in the presence of a base, of an alkyl aryl-H-phosphinate on a suitable oxazolidine of formula (A). This strategy was previously described in the review "Organic and Biomo- For example, the heterocyclic derivatives 3 with $R^1$, $R^2$, $R^3$, $R^4$ and $R^5$=H; R' =H and A=aryl or heteroaryl, were able to be obtained using a two-step reaction sequence. The first step consisted of condensation-cyclisation of methyl hypophosphite on 2,2,4,4-tetramethyl-1,3-oxazolidine, to produce H-oxazaphosphinane 5. This derivative with P—H bond was then converted via palladium-catalysed arylation to 2-aryl-oxazaphosphinane derivatives 3 (Scheme 3). Subsequent conversions in the presence of hydrogen of compounds 3 carrying aryl repeat units such as Ar=m-$NO_2$—$C_6H_4$ and p-CBzNH-$C_6H_4$, gave products 6 and 7 carrying a $NH_2$ group. From compound 3 (Ar=m-$ClC_6H_4$), a methylation reaction with methyl iodide gave the derivative N-methyl oxazaphosphinane 8, and use of Lawesson's reagent gave the thiono compound 9 (Scheme 3).

Scheme 3. Preparation of [1,4,2]-oxazaphosphinanes 3 to 9.

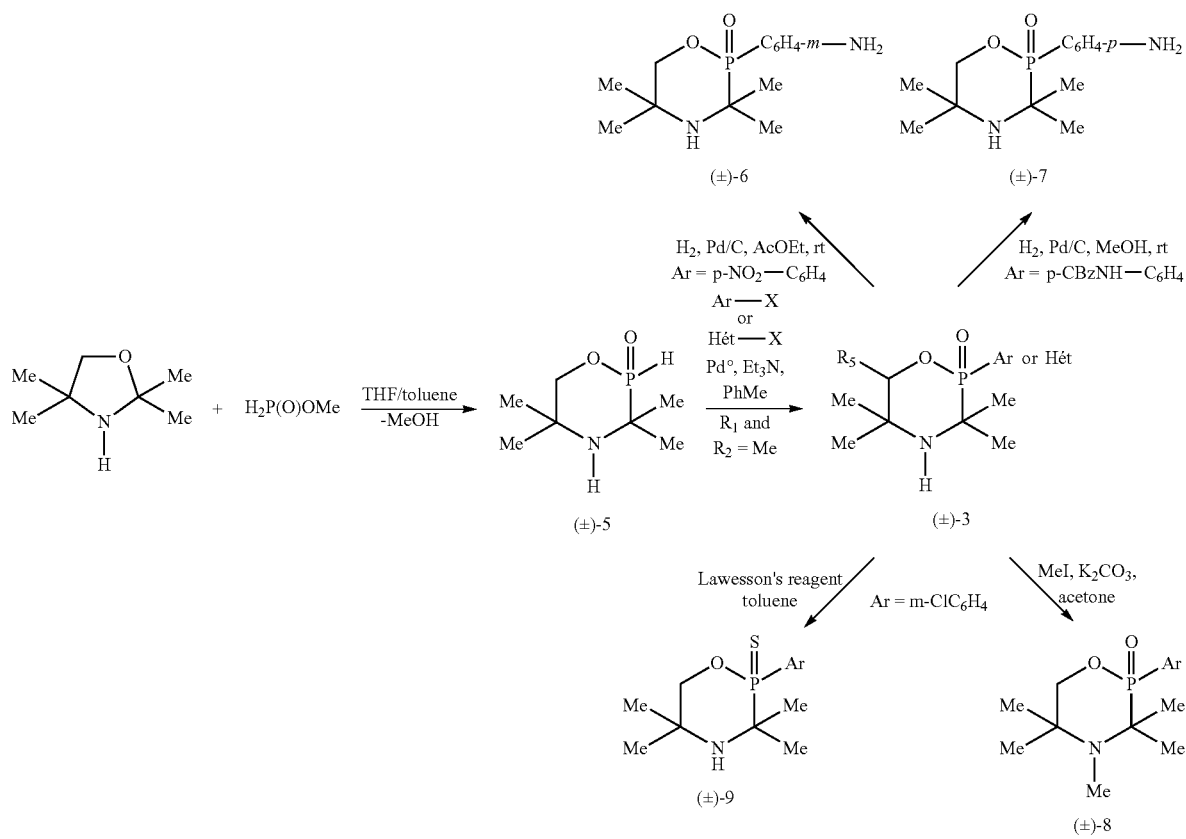

Materials and Methods

The solvents and chemical products used in the reactions were obtained from suppliers such as CARLO ERBA, Sigma-Aldrich, Alfa Aesar, Acros, . . . .

To conduct these reactions, the solvents were dried, distilled and stored in a nitrogen atmosphere. All the reactions using air- or humidity sensitive reagents were performed in a nitrogen atmosphere using glassware dried by vacuum heating. Melting points were not corrected. Nuclear Magnetic Resonance (NMR) spectra were obtained on a Bruker spectrometer (400 MHz), operating at a frequency of 400.1 MHz for $^1$H, 100.6 MHz for $^{13}$C, 162.0 MHz for $^{31}$P and 376.5 MHz for $^{19}$F. The chemical shifts δ of each nucleus are expressed in ppm, coupling constants in Hz. For the $^1$H spectra, the chloroform signal was calibrated at 7.26 ppm and 2.50 ppm for dimethylsulfoxide. For the $^{13}$C spectra, the deuterated chloroform carbon signal was calibrated at 77.16 ppm and 39.52 ppm for dimethylsulfoxide-$d_6$. All NMR experiments performed on the phosphorus nucleus or fluorine nucleus are given without hydrogen coupling. A SYNAPT G2-S mass spectrometer by Water was used to obtained High Resolution Mass Spectra (HRMS).

Example 1: Preparation of (±)-2-(3-Chlorophenyl)-2-oxo-3,3,5,5-tetramethyl-[1,4,2]-oxazaphosphinane (3b)

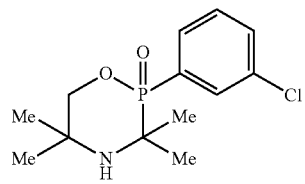 [SMILES: CC1(C)COP(=O)(c2cccc(Cl)c2)C(C)(C)N1]

The synthesis of this compound is notably described in the article: Volle, J.-N., Kaloyanov, N., Saada, M. C., Virieux, D., Pirat, J.-L. Tetrahedron lett. 2007, 48, 4695-46972.

$^1$H NMR (DMSO-$d_6$) δ 0.97 (3H, d, J=16.5 Hz), 1.07 (3H, s), 1.23 (3H, d, J=14.2 Hz), 1.29 (3H, s), 4.00 (1H, dd, J=14.9 Hz, J=11.1 Hz), 4.22 (1H, dd, J=11.2 Hz, J=5.7 Hz), 7.56-7.61 (1H, m), 7.70-7.73 (1H, m), 7.76-7.80 (2H, m). $^{13}$C NMR (DMSO-$d_6$) δ 26.93, 26.98, 27.03, 27.47 (s), 49.99 (d, J=4.4 Hz), 50.17 (d, J=92.2 Hz), 72.82 (d, J=5.9 Hz), 130.53, 130.56, 130.62, 130.68, 131.13 (d, J=10.2 Hz), 131.97 (d, J=115.6 Hz), 132.30 (d, J=2.9 Hz), 133.44 (d, J=15.4 Hz). $^{31}$P NMR (DMSO-$d_6$) δ 35.35 (s). HRMS ES+: m/z calculated for $C_{13}H_{20}ClNO_2P$ [M+H]$^+$: 288.0920; found: 288,0917.

Typical Procedure for Preparing 2-aryl-2-oxo-3,3,5,5-tetramethyl-[1,4,2]-oxazaphosphinanes At ambient temperature, aryl bromide or aryl iodide (1.5 eq.), tris(dibenzylideneacetone)dipalladium(0) (Pd$_2$(dba)$_3$, 0.05 eq.), 1,1'-bis(diphenylphosphino)ferrocene (dppf, 0.1 eq.) and triethylamine (3 eq.) were successively added to a toluene solution (10.0 mL) containing 2-oxo-3,3,5,5-tetramethyl-[1,4,2]-oxazaphosphinane (5, 2.46 mmol or 2.82 mmol; for compound 3i: 5, 3.89 mmol and toluene 13 mL). The reaction mixture was agitated and heated to 70° C. overnight. After cooling, the mixture was filtered through Celite and the Celite washed with ethyl acetate. The filtrates were combined and concentrated in vacuo. The residue obtained was then purified.

Example 2: Preparation of (±)-2-(2-Chlorophenyl)-2-oxo-3,3,5,5-tetramethyl-[1,4,2]-oxazaphosphinane (3a)

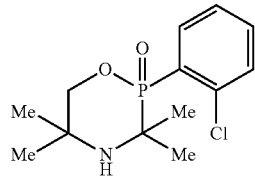 [SMILES: CC1(C)COP(=O)(c2ccccc2Cl)C(C)(C)N1]

From compound 5 (2.82 mmol) and 1-bromo-2-chlorobenzene, and after purification on C18 chromatography column, product 3a was obtained; m=144 mg, F.=168.8-169.9° C. $^1$H NMR (CDCl$_3$) δ 1.13 (3H, s), 1.16 (3H, d, J~18 Hz), 1.40 (3H, s), 1.48 (3H, d, J=14.9 Hz), 1.82 (1H, s broadened), 4.01 (1H, dd, J=15.2 Hz, J=11.1 Hz), 4.48 (1H, dd, J=11.2 Hz, J=4.7 Hz), 7.34-7.39 (1H, m), 7.44-7.47 (2H, m), 7.98-8.02 (1H, m). $^{13}$C NMR (CDCl$_3$) δ 26.05 (d, J=12.4 Hz), 26.65 (s), 28.24 (s), 28.53 (d, J=2.9 Hz), 50.33 (d, J=4.4 Hz), 51.97 (d, J=90.0 Hz), 73.17 (d, J=5.1 Hz), 126.66 (d, J=9.5 Hz), 128.57 (d, J=118.6 Hz), 131.14 (d, J=8.0 Hz), 133.53 (d, J=2.9 Hz), 135.45 (d, J=5.1 Hz), 137.12 (d, J=7.3 Hz). $^{31}$P NMR (CDCl$_3$) δ 35.08 (s). HRMS ES+: m/z calculated for C$_{13}$H$_{20}$ClNO$_2$P [M+H]$^+$: 288.0920; found: 288.0921.

Example 3: Preparation of (±)-2-(4-Chlorophenyl)-2-oxo-3,3,5,5-tetramethyl-[1,4,2]-oxazaphosphinane (3c)

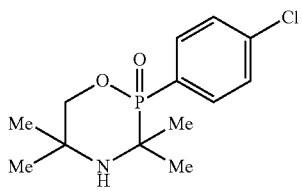 [SMILES: CC1(C)COP(=O)(c2ccc(Cl)cc2)C(C)(C)N1]

From compound 5 (2.82 mmol) and 4-chloro-1-iodobenzene, and after purification on C18 chromatography column, product 3c was obtained; m=196 mg, F.=139.8-140.4° C. RMN-$^1$H (CDCl$_3$) δ 1.10 (3H, d, J=16.2 Hz), 1.14 (3H, s), 1.31 (3H, d, J=14.4 Hz), 1.42 (3H, s), 1.76 (1H, s broadened), 3.99 (1H, dd, J=15.5 Hz, J=11.2 Hz), 4.48 (1H, dd, J=4.6 Hz, J=11.4 Hz), 7.45-7.48 (2H, m), 7.78-7.82 (2H, m). $^{13}$C NMR (CDCl$_3$) δ 26.66 (d, J=11.0 Hz), 27.01 (s), 27.37 (d, J=2.2 Hz), 28.48 (s), 50.59 (d, J=5.1 Hz), 50.83 (d, J=91.5 Hz), 73.53 (d, J=5.1 Hz), 127.19 (d, J=122.2 Hz), 128.98 (d, J=12.4 Hz), 133.57 (d, J=10.2 Hz), 139.29 (d, J=2.9 Hz). $^{31}$P NMR (CDCl$_3$) δ 36.68 (s). HRMS ES+: m/z calculated for C$_{13}$H$_{20}$NO$_2$PCl [M+H]$^+$: 288.0920; found: 288.0920.

Example 4: Preparation of (±)-2-(3,5-Dichlorophenyl)-2-oxo-3,3,5,5-tetramethyl-[1,4,2]-oxazaphosphinane (3d)

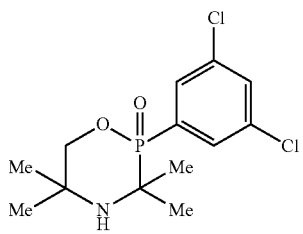 [SMILES: CC1(C)COP(=O)(c2cc(Cl)cc(Cl)c2)C(C)(C)N1]

From compound 5 (2.46 mmol) and 1-bromo-3,5-dichlorobenzene, and after purification on silica gel chromatography column, product 3d was obtained; m=600 mg, F.=177.0-177.8° C. $^1$H NMR (CDCl$_3$) δ 1.13 (3H, s), 1.13 (3H, d, J=16.2 Hz), 1.32 (3H, d, J=14.6 Hz), 1.42 (3H, s), 1.76 (1H, s broadened), 4.01 (1H, dd, J=15.4 Hz, J=11.4 Hz), 4.47 (1H, dd, J=11.1 Hz, J=3.3 Hz), 7.54 (1H, t, J=1.8 Hz), 7.71 (2H, dd, J=1.5 Hz, J=10.4 Hz). $^{13}$C NMR (CDCl$_3$), δ 26.62 (d, J=11.0 Hz), 27.03 (s), 27.34 (s), 28.41 (s), 50.60, 50.63 and 51.52, 73.87 (d, J=4.4 Hz), 130.24 (d, J=10.2 Hz), 132.65 (s), 132.74 (d, J=116.4 Hz), 135.79 (d, J=16.8 Hz). $^{31}$P NMR (CDCl$_3$) δ 34.93 (s); HRMS ES+: m/z calculated for C$_{13}$H$_{19}$Cl$_2$NO$_2$P [M+H]$^+$: 322.0530; found: 322.0533.

Example 5: Preparation of (±)-2-(2,3-Dichlorophenyl)-2-oxo-3,3,5,5-tetramethyl-[1,4,2]-oxazaphosphinane (3e)

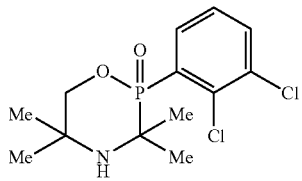 [SMILES: CC1(C)COP(=O)(c2cccc(Cl)c2Cl)C(C)(C)N1]

From compound 5 (2.46 mmol) and 1-bromo-2,3-dichlorobenzene, and after purification on silica gel chromatography column, product 3e was obtained; m=260 mg, F.=163.8-164.5° C. $^1$H NMR (CDCl$_3$) δ 1.14 (3H, s), 1.16 (3H, d), 1.39 (3H, s), 1.49 (3H, d, J=15.2 Hz), 1.81 (1H, s broadened), 4.01 (1H, dd, J=15.2 Hz, J=11.1 Hz), 4.48 (1H, dd, J=11.1 Hz, J=4.5 Hz), 7.31 (1H, td, J=7.8 Hz, J=2.8 Hz), 7.62-7.65 (1H, m), 7.93 (1H, ddd, J=9.6 Hz, J=7.8 Hz, J=1.5 Hz). $^{13}$C NMR (CDCl$_3$) δ 260.9 (d, J=12.4 Hz), 26.66 (s), 28.24 (s), 28.69 (d, J=2.9 Hz), 50.43 (d, J=5.1 Hz), 52.30 (d, J=90.0 Hz), 73.58 (d, J=5.1 Hz), 127.56 (d, J=10.2 Hz), 131.39 (d, J=114.9 Hz), 133.68 (d, J=4.4 Hz), 134.38 (d, J=2.2 Hz), 134.96, 135.08, 135.19, 135.27. $^{31}$P NMR (CDCl₃) δ 34.38 (s). HRMS ES+: m/z calculated for C₁₃H₁₉Cl₂NO₂P [M+H]⁺: 322.0530; found: 322.0530.

Example 6: Preparation of (±)-2-(3-Fluorophenyl)-2-oxo-3,3,5,5-tetramethyl-[1,4,2]-oxazaphosphinane (3f)

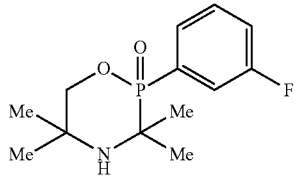 [SMILES: CC1(C)COP(=O)(c2cccc(F)c2)C(C)(C)N1]

From compound 5 (2.46 mmol) and 1-bromo-3-fluorobenzene (heated 48 h at 70° C.), and after purification on silica gel chromatography column, product 3f was obtained; m=213 mg, F.=135.3-136.1° C. ¹H NMR (CDCl₃) δ 1.12 (3H, d), 1.14 (3H, s), 1.33 (3H, d, J=14.4 Hz), 1.42 (3H, s), 1.76 (1H, s broadened, NH), 4.00 (1H, dd, J=15.4 Hz, J=11.4 Hz), 4.49 (1H, dd, J=11.4 Hz, J=4.0 Hz), 7.23-7.28 (1H, m), 7.44-7.50 (1H, m), 7.53-7.58 (1H, m), 7.63-7.67 (1H, m). ¹³C NMR (CDCl₃) δ 26.67 (d, J=11.0 Hz), 27.04 (s), 27.37 (d, J=1.5 Hz), 28.47 (s), 50.63 (d, J=4.4 Hz), 50.93 (d, J=91.5 Hz), 73.59 (d, J=4.4 Hz), 119.01 (dd, J=22.3 Hz, J=9.9 Hz), 119.78 (dd, J=21.2 Hz, J=2.2 Hz), 127.96 (dd, J=8.8 Hz, J=3.7 Hz), 130.56 (dd, J=14.3 Hz, J=7.7 Hz), 131.41 (dd, J=119.3 Hz, J=5.9 Hz), 162.56 (dd, J=250.3 Hz, J=16.8 Hz). ³¹P NMR (CDCl₃) δ 35.97 (s). ¹⁹F NMR (CDCl₃) δ -111.21 (s). HRMS ES+: m/z calculated for C₁₃H₂₀FNO₂P [M+H]⁺: 272.1216; found: 272.1217.

Example 7: Preparation of (±)-2-(4-Fluorophenyl)-2-oxo-3,3,5,5-tetramethyl-[1,4,2]-oxazaphosphinane (3g)

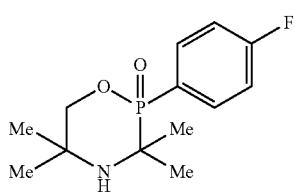 [SMILES: CC1(C)COP(=O)(c2ccc(F)cc2)C(C)(C)N1]

From compound 5 (2.82 mmol) and 1-bromo-4-fluorobenzene, and after purification on C18 chromatography column, product 3g was obtained; m=227 mg, F.=135.7-136.4° C. ¹H.NMR (CDCl₃) δ 1.10 (3H, d, J=15.9 Hz), 1.14 (3H, s), 1.31 (3H, d, J=14.4 Hz), 1.42 (3H, s), 1.76 (1H, s broadened), 3.99 (1H, dd, J=15.4 Hz, J=11.4 Hz), 4.49 (1H, dd, J=11.4 Hz, J=4.8 Hz), 7.15-7.20 (2H, m), 7.84-7.91 (2H, m). ¹³C NMR (CDCl₃) δ 26.64 (d, J=11.0 Hz), 26.96 (s), 27.32 (d, J=2.2 Hz), 28.42 (s), 50.52 (d, J=4.4 Hz), 50.75 (d, J=91.5 Hz), 73.46 (d, J=4.4 Hz), 115.93 (dd, J=21.2 Hz, J=13.2 Hz), 124.64 (dd, J=124.4 Hz, J=3.7 Hz), 134.68 (dd, J=10.2 Hz, J=8.8 Hz), 165.52 (dd, J=253.9 Hz, J=3.7 Hz). ³¹P NMR (CDCl₃) δ 36.71 (s). ¹⁹F NMR (CDCl₃) δ -105.58 (s). HRMS ES+: m/z calculated for C₁₃H₂₀FNO₂P [M+H]⁺: 272.1216; found: 272.1217.

Example 8: Preparation of (±)-2-(3-Nitrophenyl)-2-oxo-3,3,5,5-tetramethyl-[1,4,2]-oxazaphosphinane (3h)

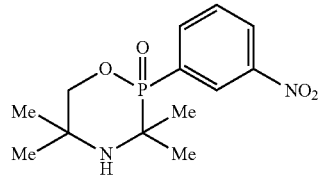 [SMILES: CC1(C)COP(=O)(c2cccc([N+](=O)[O-])c2)C(C)(C)N1]

From compound 5 (2.82 mmol) and 1-bromo-3-nitrobenzene, and after purification on silica gel chromatography column, product 3h was obtained; m=531 mg, F.=131.9-132.7° C. ¹H NMR (DMSO-d₆) δ 0.97 (3H, d, J=16.7 Hz), 1.10 (3H, s), 1.27 (3H, d, J=14.2 Hz), 1.31 (3H, s), 2.57 (1H, d broadened, J=5.6 Hz), 4.05 (1H, dd, J=15.0 Hz, J=11.2 Hz), 4.26 (1H, dd, J=11.1 Hz, J=6.1 Hz), 7.85 (2H, td, J=7.8 Hz, J=3.0 Hz), 8.23-8.27 (1H, m), 8.45-8.54 (2H, m). ¹³C NMR (DMSO-d₆) δ 26.83 (d, J=2.9 Hz), 27.00 (d, J=9.5 Hz), 27.13 (s), 27.45 (s), 50.10 (d, J=4.4 Hz), 50.30 (d, J=93.0 Hz), 73.02 (d, J=5.1 Hz), 126.39 (d, J=10.2 Hz), 127.07 (d, J=2.2 Hz), 130.49 (d, J=11.7 Hz), 131.59 (d, J=116.4 Hz), 138.20 (d, J=8.8 Hz), 147.61 (d, J=13.2 Hz). ³¹P NMR (DMSO-d₆) δ 35.41 (s). HRMS ES+: m/z calculated for C₁₃H₂₀N₂O₄P [M+H]⁺: 299.1161; found: 299.1160.

Example 9: Preparation of (±)-2-(4-benzyloxycarbamoylphenyl)-2-oxo-3,3,5,5-tetramethyl-[1,4,2]-oxazaphosphinane (3i)

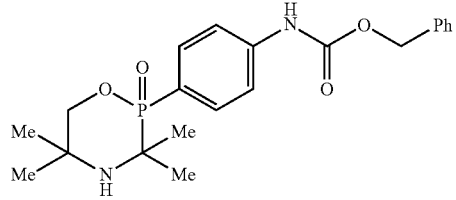 [SMILES: CC1(C)COP(=O)(c2ccc(NC(=O)OCc3ccccc3)cc2)C(C)(C)N1]

From compound 5 (3.83 mmol) and 4-bromo-benzyl phenylcarbamate, and after purification on silica gel chromatography column, product 3i was obtained; m=403 mg, F.=196.1-197.0° C. ¹H NMR (CDCl₃) δ 1.10 (3H, d, J~16.0 Hz), 1.12 (3H, s), 1.30 (3H, d, J=14.3 Hz), 1.42 (3H, s), 2.06 (1H, s broadened, NH), 3.95 (1H, dd, J=15.5 Hz, J=11.4 Hz), 4.47 (1H, dd J=11.3 Hz, J=4.3 Hz), 5.21 (s, 2H), 7.33-7.41 (5H, m), 7.52-7.54 (2H, m), 7.75-7.80 (2H, m). ¹³C NMR (CDCl₃) δ 26.51 (d, J=11.0 Hz), 26.86 (s), 27.32 (d, J=2.2 Hz), 28.28 (s), 50.51 (d, J=4.4 Hz), 50.79 (d, J=92.2 Hz), 67.07 (s), 73.27 (d, J=5.1 Hz), 118.13 (dd, J=12.4 Hz), 121.40 (dd, J=127.3 Hz), 128.33 (s), 128.39 (s), 128.63 (s), 133.10 (d, J=10.2 Hz), 135.99 (s), 142.84 (d, J=2.9 Hz), 153.49 (s). ³¹P NMR (CDCl₃) δ 37.08 (s). HRMS ES+: m/z calculated for C₂₁H₂₈N₂O₄P [M+H]⁺: 403.1787; found: 403.1789.

General Procedure for Preparing 2-heteroaryl-2-oxo-3,3,5,5-tetramethyl-[1,4,2]-oxazaphosphinanes At ambient temperature 2-oxide-3,3,5,5-tetramethyl-[1,4,2]-oxazaphosphinane [5] (5, 2.82 mmol), heteroaryl bromide (1.5 eq.), tris(dibenzylideneacetone)dipalladium(0) (Pd$_2$(dba)$_3$, 0.05 eq.), 1,1'-bis(diphenylphosphino)ferrocene (dppf, 0.1 eq.) and triethylamine (3 eq., except for 31 9 eq) are added to toluene (10.0 mL). The reaction mixture is agitated and heated to 70° C. overnight. After cooling, the mixture is filtered through Celite and the Celite washed with ethyl acetate. The filtrates are combined and concentrated in vacuo. The residue obtained is then purified.

Example 10: Preparation of (±)-2-(Pyridin-2-yl)-2-oxo-3,3,5,5-tetramethyl-[1,4,2]-oxazaphosphinane (3j)

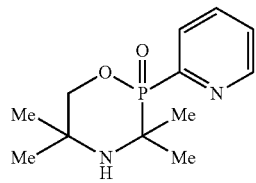 [SMILES: CC1(C)COP(=O)(c2ccccn2)C(C)(C)N1]

From 2-bromopyridine and after purification on silica gel chromatography column, product 3j was obtained; m=571 mg, F.=87.6-88.2° C. $^1$H NMR (DMSO-d$_6$) δ 0.97 (3H, d, J=16.7 Hz), 1.13 (3H, s), 1.20 (3H, s), 1.34 (3H, d, J=13.4 Hz), 2.43 (1H, s broadened), 4.15-4.20 (2H, m), 7.58-7.62 (1H, m), 7.90-8.01 (2H, m), 8.79-8.80 (1H, m). $^{13}$C NMR (DMSO-d$_6$), δ 26.42 (d, J=2.2 Hz), 26.65 (d, J=9.5 Hz), 26.95 (s), 27.13 (s), 49.91 (d, J=87.8 Hz), 50.02 (d, J=5.9 Hz), 74.55 (d, J=5.9 Hz), 126.17 (d, J=2.9 Hz), 127.60 (d, J=19.0 Hz), 136.62 (d, J=8.8 Hz), 149.97 (d, J=19.0 Hz), 153.86 (d, J=146.4 Hz). $^{31}$P NMR (DMSO-d$_6$) δ 29.13 (s). HRMS ES+: m/z calculated for C$_{12}$H$_{20}$N$_2$O$_2$P, [M+H]$^+$: 255.1262; found: 255.1264.

Example 11: Preparation of (±)-2-(Pyridin-3-yl)-2-oxo-3,3,5,5-tetramethyl-[1,4,2]-oxazaphosphinane (3k)

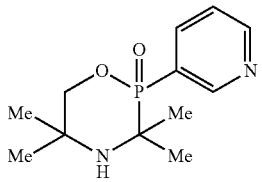 [SMILES: CC1(C)COP(=O)(c2cccnc2)C(C)(C)N1]

From 3-bromopyridine and after purification on silica gel chromatography column, product 3k was obtained; m=504 mg, F.=156.4-157.9° C. $^1$H NMR (DMSO-d$_6$) δ 0.97 (3H, d, J=16.7 Hz), 1.08 (3H, s), 1.24 (3H, d, J=14.1 Hz), 1.30 (3H, s), 4.00 (1H, dd, J=15.0 Hz, J=11.2 Hz), 4.24 (1H, dd, J=11.2 Hz, J=5.9 Hz), 7.55-7.59 (1H, m), 8.16-8.22 (1H, m), 8.79-8.81 (1H, m), 8.92-8.93 (1H, m). $^{13}$C NMR (DMSO-d$_6$) δ 26.84 (d, J=2.9 Hz), 27.01 (s), 27.02 (d, J=10.2 Hz), 27.47 (s), 50.01 (d, J=4.4 Hz), 50.17 (d, J=92.9 Hz), 72.67 (d, J=5.1 Hz), 123.71 (d, J=8.8 Hz), 125.46 (d, J=115.6 Hz), 139.89 (d, J=8.1 Hz), 151.90 (d, J=11.0 Hz), 152.90 (s). $^{31}$P NMR (DMSO-d$_6$) δ 35.37 (s). HRMS ES+: m/z calculated for C$_{12}$H$_{20}$N$_2$O$_2$P, [M+H]$^+$: 255.1262; found: 255.1264.

Example 12: Preparation of (±)-2-(Pyridin-4-yl)-2-oxo-3,3,5,5-tetramethyl-[1,4,2]-oxazaphosphinane (3l)

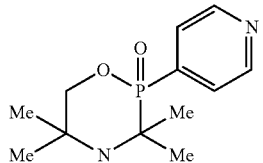

From hydrochlorinated 4-bromopyridine and after purification on silica gel chromatography column, product 31 was obtained; m=354 mg, F.=152.2-153.1° C. $^1$H NMR (DMSO-d$_6$) δ 0.97 (3H, d, J=16.7 Hz), 1.08 (3H, s), 1.25 (3H, d, J=14.4 Hz), 1.29 (3H, s), 4.02 (1H, dd, J=14.8 Hz, J=11.2 Hz), 4.23 (1H, dd, J=11.4 Hz, J=6.1 Hz), 7.73-7.77 (2H, m), 8.76-8.79 (2H, m). $^{13}$C NMR (DMSO-d$_6$) δ 26.81, 26.89, 26.91, 27.39, 49.99 (d, J=5.1 Hz), 50.06 (d, J=91.5 Hz), 72.92 (d, J=5.1 Hz), 125.66 (d, J=8.0 Hz), 138.00 (d, J=112.0 Hz), 149.87 (d, J=9.5 Hz). $^{31}$P NMR (DMSO-d$_6$) δ 34.55 (s). HRMS ES+: m/z calculated for C$_{12}$H$_{20}$N$_2$O$_2$P [M+H]$^+$: 255.1262; found: 255.1265.

Example 13: Preparation of (±)-2-(Pyrimidin-2-yl)-2-oxo-3,3,5,5-tetramethyl-[1,4,2]-oxazaphosphinane (3m)

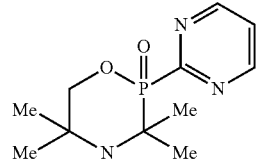

From 2-bromopyrimidine and after purification on silica gel chromatography column, product 3m was obtained; m=594 mg, F.=116.1-117.2 OC. $^1$H NMR (DMSO-d$_6$) δ 1.08 (3H, d, J=16.4 Hz), 1.14 (6H, s), 1.38 (3H, d, J=13.6 Hz), 4.19 (2H, d, J=9.9 Hz), 7.69 (1H, td, J=4.9 Hz, J=3.3 Hz), 8.99 (2H, dd, J=5.1 Hz, J=0.8 Hz). $^{13}$C NMR (DMSO-d$_6$) δ 26.32, 26.43, 26.45, 26.78, 27.08, 49.88 (d, J=5.1 Hz), 50.14 (d, J=88.6 Hz), 75.44 (d, J=6.6 Hz), 123.00 (d, J=2.9 Hz), 156.99 (d, J=13.9 Hz), 164.69 (d, J=176.4 Hz). $^{31}$P NMR (DMSO-d$_6$) δ 26.62 (s). HRMS ES+: m/z calculated for C$_{11}$H$_{19}$N$_3$O$_2$P [M+H]$^+$: 256.1215; found: 256.1217.

Example 14: Preparation of (±)-2-(Pyrimidin-5-yl)-2-oxo-3,3,5,5-tetramethyl-[1,4,2]-oxazaphosphinane (3n)

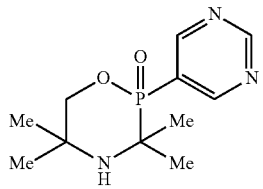

From 5-bromopyrimidine and after purification on silica gel chromatography column, product 3n was obtained; m=600 mg, F.=140.2-141.1° C. $^1$H NMR (DMSO-d$_6$) δ 1.03 (3H, d, J=17.2 Hz), 1.09 (3H, s), 1.29 (3H, d, J=14.4 Hz), 1.29 (3H, s), 2.63 (1H, d broadened, J=4.8 Hz), 4.04 (1H, dd, J=14.9 Hz, J=11.4 Hz), 4.24 (1H, dd, J=11.4 Hz, J=6.3 Hz), 9.14 (2H, d, J=4.8 Hz), 9.42 (1H, d, J=3.0 Hz). $^{13}$C NMR (DMSO-d$_6$) δ 26.55 (d, J=3.7 Hz), 26.81 (d, J=10.2 Hz), 27.13 (s), 27.44 (s), 50.03 (d, J=4.4 Hz), 50.30 (d, J=92.9 Hz), 72.86 (d, J=5.9 Hz), 124.03 (d, J=113.4 Hz), 159.87 (d, J=9.5 Hz), 160.86 (s). $^{31}$P NMR (DMSO-d$_6$) δ 33.82 (s). HRMS ES+: m/z calculated for $C_{11}H_{19}N_3O_2P$ [M+H]$^+$: 256.1215; found: 256.1216.

Example 15: Preparation of (±)-2-(3-aminophenyl)-2-oxo-3,3,5,5-tetramethyl-[1,4,2]-oxazaphophinane (6)

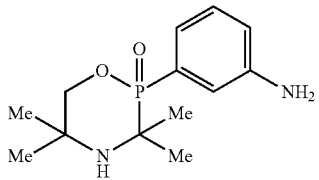 [SMILES: CC1(C)COP(=O)(c2cccc(N)c2)C(C)(C)N1]

At ambient temperature and under hydrogen atmospheric pressure, compound 3h (1.19 mmol) and palladium (10%)/C (0.025 g) were left under agitation in ethyl acetate (5.5 mL) overnight. The reaction mixture was then filtered through Celite and the Celite rinsed with dichloromethane. The filtrates were combined and concentrated. The reaction product was purified on silica gel chromatography column to give product 6; m=191 mg, F.=140.3-141.1° C. $^1$H.NMR (DMSO-d$_6$) δ 0.96 (3H, d, J=15.7 Hz), 1.03 (3H, s), 1.16 (3H, d, J=13.9 Hz), 1.28 (3H, s), 2.28 (1H, s broadened), 3.91 (1H, dd, J=14.5 Hz, J=11.2 Hz), 4.19 (1H, dd, J=10.9 Hz, J=5.1 Hz), 5.36 (2H, s), 6.73-6.75 (1H, m), 6.85-6.90 (1H, m), 7.00-7.03 (1H, m), 7.11-7.16 (1H, m). $^{13}$C NMR (DMSO-d$_6$) δ 26.73, 27.00, 27.12, 27.52, 49.98 (d, J=3.7 Hz), 50.01 (d, J=90.2 Hz), 72.37 (d, J=5.1 Hz), 116.64 (d, J=10.3 Hz), 117.34 (d, J=2.2 Hz), 118.64 (d, J=9.5 Hz), 128.93 (d, J=13.9 Hz), 129.41 (d, J=119.6 Hz), 148.65 (d, J=13.9 Hz). $^{31}$P NMR (DMSO-d$_6$) δ 37.11 (s). HRMS ES+: m/z calculated for $C_{13}H_{22}N_2O_2P$ [M+H]$^+$: 269.1419; found: 269.1420.

Example 16: Preparation of (±)-2-(4-aminophenyl)-2-oxo-3,3,5,5-tetramethyl-[1,4,2]-oxazaphosphinane (7)

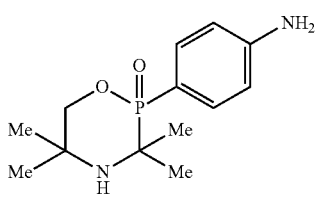 [SMILES: CC1(C)COP(=O)(c2ccc(N)cc2)C(C)(C)N1]

At ambient temperature and under hydrogen atmospheric pressure, compound 3i (0.75 mmol) and palladium (10%)/C (0.017 g) were left under agitation in methanol (3.5 mL) overnight. The reaction mixture was filtered through Celite and the Celite rinsed with dichloromethane. The filtrates were combined and concentrated. The reaction product was purified on silica gel chromatography column to give product 7; m=160 mg, F.=160.3-161.1° C. $^1$H NMR (CDCl$_3$) b 1.10 (3H, s), 1.11 (3H, d, J=15.7 Hz), 1.27 (3H, d, J=14.2 Hz), 1.40 (3H, s), 1.75 (1H, s broadened, 3.93 (1H, dd, J=15.5 Hz, J=11.3 Hz), 4.07 (2H, s broadened), 4.46 (1H, dd, J=11.3 Hz, J=4.7 Hz), 6.68 (2H, dd, J=8.4 Hz, J=2.6 Hz), 7.60 (2H, dd, J=10.3 Hz, J=8.4 Hz). $^{13}$C NMR (CDCl$_3$) δ 26.77 (d, J=11.0 Hz), 27.03 (s), 27.43 (d, J=2.2 Hz), 28.52 (s), 50.54 (d, J=5.1 Hz), 50.89 (d, J=92.4 Hz), 73.25 (d, J=4.4 Hz), 114.28 (d, J=13.2 Hz), 116.05 (d, J=132.0 Hz), 133.91 (d, J=11.0 Hz), 150.52 (dd, J=2.9 Hz). $^{31}$P NMR (CDCl$_3$) δ 38.17 (s). HRMS ES+: m/z calculated for $C_{13}H_{22}N_2O_2P$ [M+H]$^+$: 269.1419; found: 269.1419.

Example 17: Preparation of (±)-2-(3-chlorophenyl)-N-methyl-2-oxo-3,3,5,5-tetramethyl-[1,4,2]-oxazaphosphinane (8)

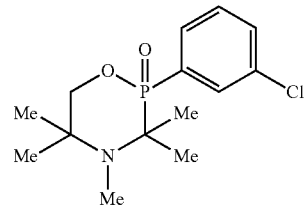 [SMILES: CN1C(C)(C)COP(=O)(c2cccc(Cl)c2)C1(C)C]

Compound 3b (1.74 mmol), potassium carbonate (3.47 mmol) and methyl iodide (3.47 mmol) were added to acetone (7.0 mL), and the mixture heated under reflux for 3 days. After cooling, the solvent was evaporated in vacuo. The reaction product obtained was purified on silica gel chromatography column to give product 8; m=270 mg, F.=144.9-145.5° C. $^1$H NMR (DMSO-d$_6$) δ 0.89 (3H, d, J=17.9 Hz), 1.04 (3H, s), 1.25 (3H, s), 1.36 (3H, d, J=12.6 Hz), 2.19 (3H, s), 3.97 (1H, dd, J=20.5 Hz, J=12.4 Hz), 4.34 (1H, dd, J=12.1 Hz, J=9.1 Hz), 7.56-7.61 (1H, m), 7.70-7.73 (1H, m), 7.80-7.85 (2H, m). $^{13}$C NMR (DMSO-d$_6$) δ 19.42 (d, J=2.9 Hz), 21.44 (s), 25.23 (s), 25.31 (s), 26.91 (d, J=11.7 Hz), 53.98 (d, J=108.3 Hz), 54.95 (s), 71.50 (d, J=5.1 Hz), 130.54 (d, J=13.2 Hz), 131.31 (d, J=8.1 Hz), 131.69 (d, J=126.6 Hz), 131.95 (d, J=9.5 Hz), 132.53 (d, J=2.2 Hz), 133.26 (d, J=15.4 Hz). $^{31}$P NMR (DMSO-d$_6$) δ 43.21 (s). HRMS ES+: m/z calculated for $C_{14}H_{22}ClNO_2P$ [M+H]$^+$: 302.1077; found: 302.1053.

Example 18: Preparation of (±)-2-(3-chlorophenyl)-2-thiono-3,3,5,5-tetramethyl-[1,4,2]-oxazaphosphinane (9)

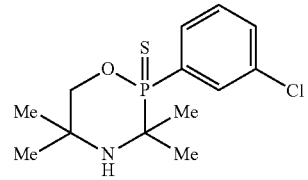 [SMILES: CC1(C)COP(=S)(c2cccc(Cl)c2)C(C)(C)N1]

In a nitrogen atmosphere, 2-(3-dichlorophenyl)-3,3,5,5-tetramethyl-2-oxo-[1,4,2]-oxazaphosphinane (3b, 3.48 mmol), Lawesson's reagent (3.49 mmol) and toluene (17 mL) were agitated and heated to 95° C. for 21 h. The solution was then cooled and the supernatant collected. The remaining paste was rinsed with toluene and the organic phases combined and evaporated. The residue obtained was purified on silica gel chromatography column to give product 9; m=171 mg, F.=103.9-104.8° C. $^1$H NMR (CDCl$_3$) δ 1.13 (3H, s), 1.18, 1.22, 1.23 and 1.27 (6H), 1.42 (3H, s), 1.99 (1H, s broadened), 3.94 (1H, dd, J=18.6 Hz, J=11.2 Hz), 4.64 (1H, dd, J=11.2 Hz, J=6.9 Hz), 7.39-7.44 (1H, m), 7.49-7.52 (1H, m), 7.78-7.83 (1H, m), 7.88-7.92 (1H, m). $^{13}$C NMR (CDCl$_3$) δ 25.81 (d, J=10.3 Hz), 27.39 (s), 28.77 (s), 28.96 (d, J=8.1 Hz), 50.35 (d, J=4.4 Hz), 54.38 (d, J=61.6 Hz), 72.45 (d, J=5.1 Hz), 129.69 (d, J=10.3), 129.91 (d, J=13.9 Hz), 131.30 (d, J=11.0 Hz), 132.33 (d, J=2.9 Hz), 134.25 (d, J=92.4 Hz), 134.94 (d, J=16.1 Hz). $^{31}$P NMR (CDCl$_3$) δ 90.12 (s). HRMS ES+: m/z calculated for $C_{13}H_{20}ClNOPS$ [M+H]$^+$: 304.0692; found: 304.0694.

Action of the Compounds

A. Materials and Methods

1. Animals

Male mice (RjOrl:SWISS) from Janvier laboratories (Le Genest-Saint-Isle, France), aged 7-9 weeks and weighing 32±2 g were used for this study. The animals were grouped in plastic cages with free access to the open field and water, in a regulated environment (23±1° C., humidity 40-60%, 12 h light/dark cycle).

2. Compounds and Peptides

The compounds were solubilized in physiological saline solution (0.9% NaCl) or in dimethylsulfoxide (DMSO) 10% in the saline solution and administered via intraperitoneal route (IP) in a volume of 100 µl per 20 g body weight.

The amyloid-β[25-35] peptide (Aβ$_{25-35}$) and control peptide (Sc.Aβ) were obtained from Genepep (Saint-Jean-de-Vedas, France). They were solubilized in injectable distilled water at a concentration of 3 mg/ml and stored at −20° C. Before injection, the peptides were incubated at 37° C. for 4 days, which enabled the Aβ$_{25-35}$ peptide but not the Sc.Aβ, to form oligomers. They were administered via intracerebroventricular route (ICV). The animals were anesthetized by inhaling 2.5% isoflurane (TEM) and were given 3 µl of peptide solution via direct ICV route (Haley and McCormick's method). For injection a 10 µl Hamilton microsyringe was used at a flow rate of 1 µl/min.

3. Spontaneous Alternation in the Y-Maze

The animals were tested for spontaneous alternation performance in a Y-maze, an index of spatial working memory. The Y-maze was in grey PVC. Each arm was 40 cm long, 13 cm high, 3 cm wide at the base and 10 cm wide in the upper part, and converging at an equal angle. Each mouse was placed at one end of an arm and was able to move freely through the maze during an 8-min session. The series of arm entries, including any returns in the same arm were visually analysed. Alternation is defined as being consecutive entries in three different arms. The maximum number of alternations is therefore the total number of arm entries less two, and alternation percentage is calculated as (actual alternations/maximum possible alternations)×100. The parameters comprise the alternation percentage (memory index) and the total number of arm entries (exploratory index).

4. Passive Avoidance Test

The apparatus contained two compartments (15×20×15 cm in height) with one light part having walls in white PVC and the other dark with walls in black PVC and a grid floor. A vertical sliding door separated each compartment. A 60 W lamp was positioned 40 cm above the white compartment during the experiment. Electrical shocks (0.3 mA for 3 s) were delivered to the grid floor by means of a scrambled shock generator (Lafayette Instruments, Lafayette, United States). The vertical sliding door was first closed during the training session. Each mouse was placed in the white compartment. After 5 s, the door was opened. When the mouse entered the dark compartment and placed its paws on the grid floor, the door was closed and an electric shock delivered for 3 s. Step-through latency (STL) i.e. the time taken to enter the dark compartment and the number of cries, were recorded. The retention test was performed after 24 h. Each mouse was again placed in the white compartment. After 5 s, the door was opened. Step-through latency was recorded up to 300 s.

5. Spatial Learning in Pool

The pool was a circular water chamber (diameter 140 cm, height 40 cm). Water temperature, 22-24° C., light intensity, external reference points in the room and water opacity were strictly reproduced. A non-slip transparent platform in plexiglass (diameter 10 cm) was immersed under the surface of the water during acquisition. Swims could be recorded using Videotrack® ViewPoint software, (Champagne-au-Mont-d'Or, France), with trajectories analysed for time and distance. The software divides the pool into four quadrants.

Acquisition phase: this consisted of 3 swims per day for 5 days with an interval of 20 min. The starting positions were fixed at the cardinal points delimiting the quadrants and selected randomly. Each animal was given 90 s to find the platform. Swim latency was measured. The animals were left on the platform for 20 s. The animals which did not find the platform after 90 s were placed thereupon manually and left for 20 s. The median of swim times was calculated for each day and expressed for the experimental group as a mean±SEM.

Recall phase: a trial test was conducted 24 h after the last acquisition session. The platform was removed and each animal swam for 60 s. The session was monitored by video and the time spent in the training quadrant (where the platform had been placed) was measured.

6. Object Recognition Test

The apparatus consisted of four square-shaped arenas (50 cm×50 cm×50 cm in height) made of white plexiglass and placed on a platform equipped with infrared light-emitting diodes (IR). The locomotor activity of the animal and position of the nose were able to be captured by an IR-sensitive camera and analysed using Videotrack and Nose-track software. On Day 1, the animals were acclimatized for 10 min to the open field. On Day 2, two identical objects (plastic bottles with stopper) were placed at defined positions at and of a diagonal plane of the arena. Each mouse was placed in the open field and exploratory activity and nose position were recorded for 10 min. Activity was analysed in terms of number of contacts with the objects and contact time. On Day 3, the object at position 2 was replaced by a novelty (chair leg protections in black plastic) differing in shape, colour and texture from the familiar object. Each mouse was again placed in the open field and exploratory activity recorded for 10 min. Activity was analysed in similar manner. The exploratory preference index was calculated as the ratio between the number (or time) of contacts with the object at position 2 and the total number (or time) of contacts with the two objects. The animals which showed fewer than 10 contacts with the objects during sessions 2 and 3 were generally excluded from calculations.

7. Measurements of Oxidative Stress

After sacrifice, the hippocampus and brain cortex of the mice were dissected and frozen to −80° C. until use. The accumulation of reactive oxygen species was measured by fluorescence of 2',7'-dichlorofluorescein (DCF) in the hippocampus of the mice ex vivo. DCF diacetate (0.5 µM) (Sigma-Aldrich) was added to SDS-soluble fractions of hippocampus extract. After 30 min at 37° C., DCF fluorescence was quantified (excitation at 485 nm, emission at 530 nm) in a Fluoroskan Ascent spectrofluorometer (Thermo Scientific, Waltham, USA), and normalized with the protein concentrations of the extracts.

Peroxidation of membrane lipids was measured using the cumene/xylenol method. The hippocampi were homogenized in methanol (1:10), centrifuged at 1 000 g for 5 min and the supernatant collected. Aliquots were added to a solution containing 1 mM $FeSO_4$, 0.25 m $H_2SO_4$, 1 mM xylenol orange and incubated for 30 min at ambient temperature. Absorbance was measured at 580 nm ($A_{580}1$), then 10 µl of 1 mM cumene hydroperoxide (CHP) was added and the sample incubated 30 min at ambient temperature. Absorbance was measured at 580 nm ($A_{580}2$). Lipid peroxidation level was determined as CHP equivalents: CHP eq.=$A_{580}1$/$A_{580}2$×[CHP (nmol)]×dilution, and calculated in CHP eq. per tissue weight expressed as % of the control group.

8. Measurement of Expression Levels of Bax, Bcl-2, TNFα, IL-1β and Synaptophysin The hippocampi were homogenized in 50 mM Tris-150 mM NaCl solution, pH 7.5, and sonicated for 20 s. After centrifugation at 16 100 g for 15 min at 4° C., the supernatants were used for ELISA assays in accordance with the manufacturer's instructions (ThermoScientific, Courtaboeuf, France; USCN, Wuhan, China). For each assay, absorbance was read at 450 nm and the concentration of each sample calculated in comparison with a standard curve. The results are expressed in ng or pg per mg of tissue and expressed as % of the control group.

19. Statistical Analyses

Data were analysed by one-factor analysis of variance (ANOVA, F statistic), followed by a Dunnet multiple comparison test. The swim times did not follow Gaussian distribution since a maximum value was applied. The acquisition profiles were therefore analysed using Friedman non-parametric ANOVA with repeated measures followed by a Dunn or Mann-Whitney test. Trial test data are given as time spent in the training quadrants (T) or in the three other quadrants as a mean (o) and analysed with a t-test in relation to the chance level (15 s). Object preference, calculated from the number of contacts or contact time with the objects, was analysed with a t-test in relation to chance level (50%). The level of statistical significance was $p<0.05$.

B. Pharmacological Results

1. Analysis of Protection Induced by Compound 3b

Compound 3b was injected via IP route, from 0.3 to 3 mg/kg, immediately before ICV injection of oligomerized $Aß_{25-35}$ peptide, an acute pharmacological model of amyloid toxicity. After one week, the animals were tested for behavioural performance, then sacrificed and the brain dissected for biochemical analyses.

On Day 7, after the injections of 3b and amyloid peptide, the mice were tested for their ability to alternate in the Y-maze, a spatial working memory test. Compared with the control animals, which had been given a non-toxic peptide (scrambled Aß, ScAß) via ICV and exhibited an alternation percentage of 65% (FIG. 1a), the $Aß_{25-35}$ animals showed a very significant deficit. Administration of compound 3b significantly prevented this deficit at doses of 0.7, 1.5 and 3 mg/kg (FIG. 1a). The treatments did not affect mobility and exploratory capabilities of the animals since the total number of explored arms during the 8 min session remained unchanged (FIG. 1b). The mice were then tested for passive avoidance response, a long-term non-spatial memory test. with training on Day 8 and recall on Day 9 after the injections (FIG. 1c). The $Aß_{25-35}$ animals showed a very significant deficit in response. All the tested doses of 3b allowed prevention of this deficit (FIG. 1c).

The dose of 0.7 mg/kg being the minimum active dose in these dose-dependent experiments, one group was injected and tested on Days 7 to 9 for object recognition. Session 1 concerned habituation to the square arena in which the test was conducted. At session 2, two identical objects were placed in the arena and the interaction time and number of contacts by the animal with the objects were measured. At session 3, one object among the two was replaced by a novel object and animal preference for this novel object was measured. Each session was separated by 24 h. The results are given as number of contacts (FIG. 1d) or interaction time (FIG. 1e). In both cases, it is noted that the control mice ScAß do not show any preference between the two identical objects at session 2, but show a significant preference for the novel object at session 3 (FIG. 1d, e). The $Aß_{25-35}$ animals do not show any preference but treatment with compound 3b restores significant preference. These results show that compound 3b protects recognition memory that had been altered in the model. Finally, it will be noted that in all cases compound 3b, at 0.7 or 3 mg/kg, does not affect the performance of the control animals ScAß.

On Day 9, the animals were sacrificed, the brains removed, the hippocampi and cortex dissected and frozen. Biochemical analyses measured the amplitude of oxidative stress, the inducing of apoptotic pathways, neuroinflammation, synaptic changes and cholinergic tonus in the animals, either by conducting colorimetric or radioactive assays, or using commercial Elisa kits. Oxidative stress was very significantly induced after injection of peptide $Aß_{25-35}$, as measured by an increase in reactive oxygen species (ROS) in the hippocampus (DCF fluorescence assay, FIG. 2a), or an increase in the level of membrane lipid peroxidation (LPO) in the cortex (FIG. 2b). Treatment with 3b, in particular at a dose of 0.7 mg/kg IP, allowed very significant blocking of ROS induction (FIG. 2a), or more efficient reduction of LPO level (FIG. 2b).

Inducing of programmed cell death pathways, apoptosis, can be measured using several markers. The so-called intrinsic pathway can be measured by an increase in the pro-apoptotic protein Bax and/or a decrease in the anti-apoptotic protein Bcl2, and hence an increase in the Bax/Bcl2 ratio. We observed a significant increase in Bax (FIG. 2c) and no change in Bcl2 (FIG. 2d) after injection of the $Aß_{25-35}$ peptide. However, the Bax/Bcl2 ratio increases most significantly (FIG. 3e). Treatment with 3b over the dose range 0.3-1.5 mg/kg IP significantly reduces the increase in Bax (FIG. 2c) and hence the ratio Bax/Bcl2 (FIG. 2e). It is to be noted that compound 3b, tested at 1.5 mg/kg IP, tends to increase Bax (FIG. 2c) and hence the Bax/Bcl2 ratio (FIG. 2e) in the control animals ScAß. The treatment has no effect on Bcl2 levels (FIG. 2d).

Neuroinflammation was analysed by measuring tissue levels of two pro-inflammatory cytokines, TNFα (FIG. 3a) and IL6 (FIG. 3b), which are known to be increased in the model. The very significant increase in TNFα was prevented by compound 3b at the dose of 0.7 mg/kg IP (FIG. 3a). The significant increase in IL6 was attenuated but non-significantly by the same dose of 3b (FIG. 5b).

Synaptic changes were evaluated by measuring the expression of the pre-synaptic scaffold protein, synaptophysin (FIG. 3c). A very significant decrease of 20% was measured, that was prevented by 3b at a dose of 0.7 mg/kg IP (FIG. 3c).

Cholinergic tonus was evaluated by measuring the activity of choline acetyltransferase, the enzyme limiting synthesis of acetylcholine. A moderate but very significant decrease was observed in the enzymatic activity of the model, that was blocked by treatment with 3b, 0.7 mg/kg Ip (FIG. 3d).

From the screening of the molecules in the series (see below), compound 3c, the isomer at Chlorine position of 3b, proved to be highly efficient. It was therefore tested over a broad dose range of 0.03 à 0.7 mg/kg IP, in the $Aβ_{25-35}$ model. The animals were tested for spontaneous alternation on Day 7, for passive avoidance on Days 8 and 9 (FIG. 4). Analysis confirmed that the dose of 0.3 mg/kg IP significantly prevents spontaneous alternation deficit induced by $Aβ_{25-35}$ (FIG. 4a), but only this dose appeared to be efficient. In parallel, a significant hyperactivity effect was measured for the total number of maze arms explored during the 8 min of the session (FIG. 4b). The doses of 0.1 and 0.3 mg/kg IP appeared effective for long-term memory response (FIG. 4c).

Finally, a first mechanistic analysis of the pharmacological effect in vivo of compound 3b was carried out. With the objective of confirming that the compound, neuroprotective against amyloid toxicity, could also be anti-amnesic in a pharmacological amnesia model, we first determined its effectiveness against the amnesic effects of scopolamine. Animals were treated with compound 3b, 0.03-1.5 mg/kg Ip, 10 min before they were given scopolamine, 0.5 mg/kg SC, an antagonist of the muscarinic cholinergic receptors. Scopolamine was injected 20 min before a memory task: measurement of spontaneous alternation in the Y-maze (FIG. 5a, b) or training for the passive avoidance test (FIG. 5c, d). It appeared that compound 3b significantly attenuates alternation deficit induced by scopolamine, at doses of 0.1 and 0.3 mg/kg IP (FIG. 5a). In parallel, at the lowest doses tested, it appears to increase the hyper-locomotor effect of scopolamine (FIG. 5b). In the long-term memory test, the compound attenuates reduced step-through latency induced by scopolamine, at the same doses of 0.1 and 0.3 mg/kg (FIG. 5c) and reduces the increase in escape latency induced by scopolamine, at all tested doses (FIG. 5d). The compound is indeed anti-amnesic and the effective dose is 0.1 mg/kg IP.

The results of CEREP profiling suggested an increase in binding of the $α_7$ nicotinic radioligand. The effect of co-administering antagonists of the nicotinic cholinergic receptors with $σ_1$ was examined on the anti-amnesic effect of compound 3b, 0.1 mg/kg IP, i.e. methyllycaconitine (MLA) for the $α_7$ nicotinic receptors, dihydro-β-erythroidine for the $α_4β_2$ nicotinic receptors and NE100 for the $σ_1$ receptors. The effects of the antagonists were examined with the two behavioural tests of spontaneous alternation and passive avoidance (FIG. 6). It appeared that MLA blocked the anti-amnesic effect of compound 3b at the dose of 3 mg/kg IP for spontaneous alternation (FIG. 6a) and attenuated the effect for passive avoidance at the dose of 1 mg/kg IP (FIG. 6b). DhβE appeared to be ineffective at the two doses tested, for spontaneous alternation (FIG. 6c) and passive avoidance (FIG. 6d). NE100, tested only at dose 1 mg/kg IP, blocked the effect of compound 3b for spontaneous alternation (FIG. 6e) and attenuated the effect for passive avoidance (FIG. 6f).

These results confirm that the anti-amnesic, and possibly neuroprotective, effects of compound 3b are based on $α_7$ nicotinic and a components.

To summarize, the above-mentioned results allow the following conclusions to be drawn:

in the non-transgenic AD model, induced by ICV injection of the $Aβ_{25-35}$ peptide in mice, compound 3b and compound 3c have neuroprotective effects at behavioural and biochemical levels. The compounds are active at low doses (0.7 and 0.3 mg/kg IP respectively) of the same order of magnitude as the reference molecules in this model: 0.5 mg/kg IP for donepezil and 1 mg/kg IP for memantine, for example. There is complete functional recovery. All the biochemical markers of toxicity examined in the model up until now i.e. oxidative stress, apoptosis, neuroinflammation, synaptic and cholinergic tonus changes, are attenuated or blocked by compound 3b at its active dose;

a first pharmacological study suggests that the anti-amnesic effects and possibly neuroprotective effects of compound 3b are based on an $α_7$ nicotinic component and $σ_1$ component. A positive allosteric modulator (PAM) profile on these two receptors is to be researched. These targets are able to act in synergy which would account for the in vivo efficacy of these compounds.

2. In Vivo Screening of Derivatives

From the molecules derived from the synthesis, a panel of 8 derivatives was selected and screened for potential neuroprotective efficacy. The compounds were injected at a dose of 0.3 mg/kg IP, i.e. the maximum non-active dose of 3b and compared with 3b injected at 0.3 and 0.7 mg/kg IP. The compounds were injected ICV immediately before the $Aβ_{25-35}$ peptide, and the mice were tested for spontaneous alternation on Day 7, passive avoidance on Days 8 and 9 and the ROS level was measured in the hippocampus (FIG. 7). For each response (spontaneous alternation: FIG. 7a; step-through latency in passive avoidance: FIG. 7b, and DCF fluorescence level: FIG. 7c), a 50% level of the effect between the values of the ScAβ and $Aβ_{25-35}$ animals was taken as criterion of efficacy. It was verified that the 3b dose of 0.7 mg/kg IP, but not 0.3, allowed this criterion to be met. Compounds 3c, 3n and 3l met the criterion for the 3 parameters. Compound 3c is an isomer at the position of the chlorine atom of 3b. Regarding compound 3n, this has a 5-pyrimidyl group attached to the phosphorus atom, and for compound 3l it is a 4-pyridinyl group. The efficacy of 3c, as effective at 0.3 mg/kg IP as 3b at 0.7 mg/kg IP, led to the selection thereof for the remainder of the study.

3. Analysis of Protection Induced by the Phosphinolactones in a Transgenic Model of the Disease TG2576 mice, over-expressing the human amyloid precursor protein carrying the Swedish double mutation $APP_{Swe}$, develop the pathology towards the age of 8-10 months and up until 15-17 months, age at which 95% of the animals show behavioural, biochemical and morphological signs of the disease. Compound 3b was administered under chronic treatment at doses of 0.7 mg/kg/d IP and then 2 mg/kg/d IP. The effect of compound 3c, at a dose of 1 mg/kg/j IP, was also documented.

The animals treated with 3b were tested for spontaneous alternation after a treatment time of 1 and 2 months (FIG. 8a). After treatment for one month, 3b does not affect the performance of the wild-type control animals (VT), but the $APP_{Swe}$ animals no longer alternate (FIG. 8a). Treatment with 3b, at 2 mg/kg/d but not at 0.7 mg/kg/d, significantly prevents alternation deficit. After treatment for 2 months, the control (WT) and APP$_{Swe}$ animals still show good alternation and a deficit respectively (FIG. 8b). The two doses of 3b attenuate the deficit in the APP$_{Swe}$ mice, but the lowest dose appears to impact alternation in the WT animals (FIG. 8b). Locomotor analysis after treatment for 1 month (FIG. 8c) or 2 months (FIG. 8d), does not show any difference between the groups of animals.

After 2-month treatment, the mice were examined with a complex long-term spatial learning test, the locating of an invisible platform in a circular pool 1.5 m in diameter, followed by the object recognition test. The pool acquisition profiles are given in FIG. 9a,b. Each test corresponded to the median value of 3 swims per day. The WT animals and WT treated with 3b, 2 mg/kg/d, efficiently acquired the principle of the test and locating of the platform (FIG. 9a). The APP$_{Swe}$ animals also showed a profile which decreased over the tests, but latencies were significantly higher than in the WT animals (FIG. 9b). Treatment with 3b tends to reduce these latencies. 48 h after the last acquisition session, the platform was withdrawn from the pool and the time spent in each of the quadrants of the pool was analysed. The results (FIG. 9c) give the time spent in the training quadrant (where the platform had been positioned) and the mean of the other quadrants. It appears that the WT animals show a very significant preferred presence in the training quadrant. The APP$_{Swe}$ mice do not show any spatial preference but treated with 3b significantly restores preferred presence in the training quadrant (FIG. 9c). However, a decrease is noted in spatial performance of the WT mice treated with 3b at 2 mg/kg/j IP, although spatial preference significantly persists.

In the object recognition test, the motivation of the animals to familiarize themselves with the objects was first analysed at sessions 2 and 3 of the test (FIG. 9d). It appears that the APP$_{Swe}$ animals show a significant decrease in the number of contacts during the 10 min sessions. This decrease is prevented by treatment with 3b, without effect in the WT animals (FIG. 9d). Analysis of object recognition gave mixed results in terms of number of contacts (FIG. 9e), but clearer in terms of contact times (FIG. 9f). It appears that while none of the groups showed a preference at session 2, the WT groups do show a preference for the novel object at session 3 (FIG. 9f). The APP$_{Swe}$ animals do not show any object preference. This deficit is attenuated, but non-significantly, by treatment with compound 3b (FIG. 9f).

In the series of experiments with compound 3c, at a dose of 1 mg/kg/d, the animals were also analysed for spontaneous alternation after a treatment time of 1 month and 2 months (FIG. 10). After treatment for 1 month, the alternation deficit observed in the APP$_{Swe}$ animals was attenuated by compound 3c (FIG. 10a). After 2 months, the more pronounced deficit in the APP$_{Swe}$ animals was significantly blocked by treatment with 3c (FIG. 10b). No locomotor effect at the Y-maze sessions was observed between the groups (FIG. 10c,d). The animals were also analysed after 2-month treatment for the pool spatial learning test and object recognition test (FIG. 11). The WT animals and WT treated with 3c, 1 mg/kg/d, efficiently acquired the principle of the test and locating of the platform (FIG. 11a). The APP$_{Swe}$ animals also showed a similar profile to the WT animals, suggesting that the memory deficit was little pronounced in this experimental group (FIG. 11b). Treatment with 3c did not affect the acquisition profile (FIG. 11b). At the trial test, 48 h after the last training, the WT animals showed a very significant preferred presence in the training quadrant (FIG. 13c). The APP$_{Swe}$ mice also showed a spatial preference that was less pronounced since the presence in the training quadrant did not significantly differ from the chance level (15 s). Treatment with compound 3c significantly restored preferred presence in the training quadrant (FIG. 11c). A decrease is noted in spatial performance in WT mice treated with 3c, although spatial preference persists significantly.

In the object recognition test, analysis of the motivation of the animals to familiarize themselves with the objects (FIG. 11d) confirmed that the APP$_{Swe}$ animals show a significant decrease in the number of contacts during the 10 min sessions. This decrease is blocked by treatment with 3c, without effect in the WT animals (FIG. 11d). Analysis of object recognition gave coherent results whether processed as number of contacts (FIG. 11e) or contact time (FIG. 11f). It appears that none of the groups shows a significant preference at session 2, even if the values of number of contacts move away from 50% (FIG. 11e). On the other hand, at session 3, the WT groups clearly show preference for the novel object (FIG. 11e,f). The APP$_{Swe}$ animals do not show any object preference. This deficit is significantly blocked or attenuated by treatment with CL420 (FIG. 11e,f).

Various biochemical parameters were analysed in the hippocampus of APP$_{Swe}$ mice after treatments with 3b, 2 mg/kg/j IP, or 3c, 1 mg/kg/j IP (FIG. 12). Treatment with 3b significantly reduced oxidative stress and TNFα level, but did not affect levels of synaptophysin, Bax and IL1ß (FIG. 12a). Treatment with 3c caused a decrease in the expression of Bax, but not in the levels of oxidative stress, synaptophysin or IL1ß (FIG. 12b).

To summarize, the effects of two phosphinolactone compounds, 3b the lead molecule, and 3c derived from pharmacological screening, were analysed by chronic treatment (2 months) in a reference transgenic mouse model for AD: APP$_{Swe}$ mice. The doses used for these compounds, 1 or 2 mg/kg/j IP, were low and of the same order of magnitude as those used for the reference molecules, e.g. donepezil or memantine, in this animal model. These active doses suggest that the bioavailability of the molecules is very good and especially indicate a mechanism of action that is particularly effective having regard to the pharmacological profile, undetermined up until now, of these molecules. The compounds are effective in preventing learning and memory deficits observed in APP$_{Swe}$ animals when conducting conventional animal cognition tests (spontaneous alternation pool spatial learning and object recognition). The biochemical results are more fragmented and, while they suggest that the two treatments are not just symptomatic, more in-depth studies are needed to determine a potential neuroprotective effect.

4. Modulation of the Sigma-1 Protein

The results in FIG. 13 show that:

Compound 3b does not compete with the sigma-1 radiotracer in preparations of guinea pig brain membranes, and therefore that the molecule does not bind to the sigma-1 protein in orthostatic manner;

Compound 3b is antidepressant in the forced swim test, and this effect is blocked by a selective pharmacological antagonist of the sigma-1 receptors and in KO mice for the sigma-1 receptor. The molecule exhibits behavioural effects of sigma-1 type.

At a dose at which the molecule is not active (5 mg/kg), combined with a dose at which igmesine (historic sigma-1 agonist) itself is not active (10 mg/kg), a significant antidepressant effect is observed. This effect is fully blocked by a selective sigma-1 antagonist.

To conclude, compound 3b acts as allosteric modulator (PAM) of sigma-1.

The invention claimed is:

1. A method of treating a neurodegenerative disease, comprising administering to a subject in need thereof an effective a compound of following formula (I):

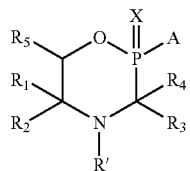

where:
X is O or S;
A is selected from the group formed by:
(C$_6$-C$_{10}$) aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, OR$_a$, SR$_a$, NO$_2$, NR$_a$R$_b$, N(R$_a$)COOR$_c$, R'$_a$ and OR'$_a$;
R$_a$ and R$_b$, the same or different, being H or (C$_1$-C$_6$) alkyl group;
R$_c$ being a —(C$_1$-C$_6$) alkylene-(C$_6$-C$_{10}$) aryl radical, in particular a —CH$_2$— (C$_6$-C$_{10}$) aryl radical;
R'$_a$ being selected from the groups CF$_3$, CHF$_2$ and CH$_2$F
R' is H or (C$_1$-C$_6$)alkyl group;
R$_1$, R$_2$, R$_3$, R$_4$ and R$_5$, the same or different, are selected from the group formed by:
H,
(C$_1$-C$_6$)alkyl groups, and
(C$_6$-C$_{10}$) aryl groups,
R$_1$ and R$_2$, together with their carrier carbon atom, able to form a spiran ring having 3 to 6 carbon atoms, and/or
R$_3$ and R$_4$, together with their carrier carbon atom, able to form a spiran ring having 3 to 6 carbon atoms.

2. The method according claim 1, wherein R' is H.

3. The method according to claim 1, wherein R$_1$, R$_2$, R$_3$ and R$_4$, the same or different, are (C$_1$-C$_6$)alkyl groups and R$_5$ is H.

4. The method according to claim 1, wherein X is O.

5. The method according to claim 1, wherein A is an optionally substituted phenyl group.

6. The method according to claim 1, wherein A is a heteroaryl having 6 atoms of which at least one is a nitrogen atom.

7. The method according to claim 6, wherein A is selected from the group formed by 2-pyridinyl, 3-pyridinyl, 4-pyridinyl, 2-pyrimidinyl and 5-pyrimidinyl groups.

8. Compound of following formula (I-1):

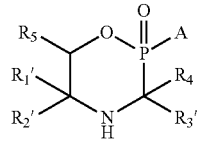

where:
R'$_1$, R'$_2$ and R'$_3$, the same or different, are (C$_1$-C$_6$) alkyl groups or (C$_6$-C$_{10}$)aryl groups, R'$_1$, R'$_2$ and R'$_3$ preferably being methyl groups;
R$_4$ and R$_5$, the same or different, are selected from the group formed by:
H,
(C$_1$-C$_6$)alkyl groups, and
(C$_6$-C$_{10}$) aryl groups,
R'$_1$ and R'$_2$, together with their carrier carbon atom, able to form a spiran ring having 3 to 6 carbon atoms, and/or
R'$_3$ and R$_4$, together with their carrier carbon atom, able to form a spiran ring having 3 to 6 carbon atoms;
is selected from the group formed by:
(C$_6$-C$_{10}$) aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, OR$_a$, SR$_a$, NO$_2$, NR$_a$R$_b$, N(R$_a$)COOR$_c$, R'$_a$ and OR'$_a$;
R$_a$ and R$_b$, the same or different, being H or (C$_1$-C$_6$) alkyl group;
R$_c$ being a —(C$_1$-C$_6$) alkylene-(C$_6$-C$_{10}$) aryl radical, in particular a —CH$_2$— (C$_6$-C$_{10}$) aryl radical;
R'$_a$ being selected from among the groups CF$_3$, CHF$_2$ and CH$_2$F;
and, when R'$_1$=R'$_2$=R'$_3$=Me, R$_4$=Me or H and R$_5$=H, A differs from the following groups:

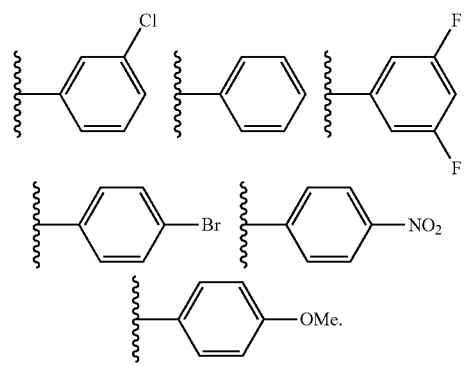

9. The compound according to claim 8, wherein A is an aromatic ring having 6 atoms, at least one of which is a nitrogen atom, or A is selected from among the following groups:

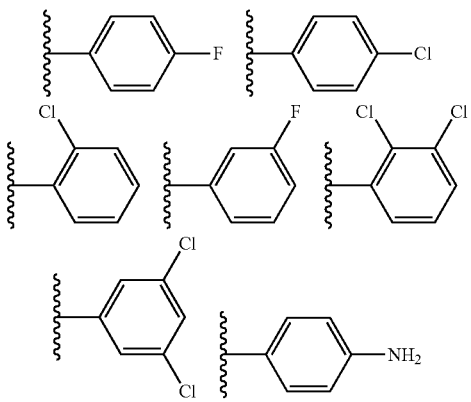

-continued

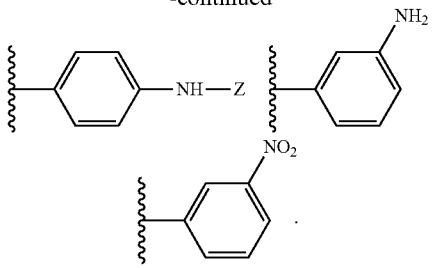

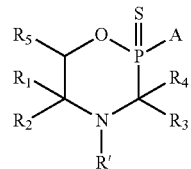

10. Compound of following formula (1-2):

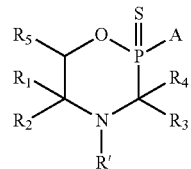

(I-2)

where:
A is selected from the group formed by:
($C_6$-$C_{10}$) aryl groups,
heteroaryl groups having 5 to 10 atoms, and,
heterocycloalkyls having 5 to 10 atoms,
said aryl, heteroaryl and heterocycloalkyl groups optionally being substituted by at least one substituent selected from the group formed by halogen atoms, $OR_a$, $SR_a$, $NO_2$, $NR_aR_b$, $N(R_a)COOR_c$, $R'_a$ and $OR'_a$;
$R_a$ and $R_b$, the same or different, being H or ($C_1$-$C_6$) alkyl group;
$R_c$ being a —($C_1$-$C_6$) alkylene-($C_6$-$C_{10}$) aryl radical, in particular a —$CH_2$— ($C_6$-$C_{10}$) aryl radical;
$R'_a$ being selected from the groups $CF_3$, $CHF_2$ and $CH_2F$;
R' is H or ($C_1$-$C_6$)alkyl group;
$R_1$, $R_2$, $R_3$, $R_4$ and $R_5$, the same or different, are selected from the group formed by:
H,
($C_1$-$C_6$)alky groups, and
($C_6$-$C_{10}$) aryl groups,
$R_1$ and $R_2$, together with their carrier carbon atom, able to form a spiran ring having 3 to 6 carbon atoms, and/or
$R_3$ and $R_4$, together with their carrier carbon atom, able to form a spiran ring having 3 to 6 carbon atoms.

11. Compound of following formula (1-3):

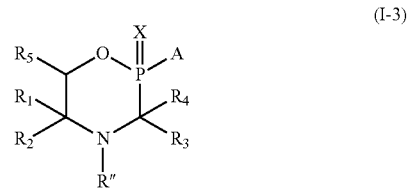

(I-3)

where:
X is O or S;
A is selected from the group formed by:
($C_6$-$C_{10}$) aryl groups,
heteroaryl groups having 5 to 10 atoms, and
heterocycloalkyls having 5 to 10 atoms,
said aryl, heteroaryl and heterocycloalkyl groups optionally being substituted by at least one substituent selected from the group formed by halogen atoms, $OR_a$, $SR_a$, $NO_2$, $NR_aR_b$, $N(R_a)COOR_c$, $R'_a$ and $OR'_a$;
$R_a$ and $R_b$, the same or different, being H or ($C_1$-$C_6$) alkyl group;
$R_c$ being a —($C_1$-$C_6$) alkylene-($C_6$-$C_{10}$) aryl radical, in particular a —$CH_2$— ($C_6$-$C_{10}$) aryl radical;
$R'_a$ being selected from the groups $CF_3$, $CHF_2$ and $CH_2F$;
R" is a ($C_1$-$C_6$) alkyl group;
$R_1$, $R_2$, $R_3$, $R_4$ and $R_5$, the same or different, are selected from the group formed by:
H,
($C_1$-$C_6$)alky groups, and
($C_6$-$C_{10}$) aryl groups,
$R_1$ and $R_2$, together with their carrier carbon atom, able to form a spiran ring having 3 to 6 carbon atoms, and/or
$R_3$ and $R_4$, together with their carrier carbon atom, able to form a spiran ring having 3 to 6 carbon atoms.

12. Pharmaceutical composition comprising at least one compound according to claim 8, in association with at least one pharmaceutically acceptable vehicle.

13. A pharmaceutical composition comprising at least one compound according to claim 9, in association with at least one pharmaceutically acceptable vehicle.

14. A pharmaceutical composition comprising at least one compound according to claim 10, in association with at least one pharmaceutically acceptable vehicle.

15. A pharmaceutical composition comprising at least one compound according to claim 11, in association with at least one pharmaceutically acceptable vehicle.

* * * * *